(12) United States Patent
Okiyama

(10) Patent No.: US 8,506,548 B2
(45) Date of Patent: Aug. 13, 2013

(54) CONNECTOR

(75) Inventor: Tadashi Okiyama, Hiroshima (JP)

(73) Assignee: JMS Co., Ltd., Hiroshima (JP)

( * ) Notice: Subject to any disclaimer, the term of this patent is extended or adjusted under 35 U.S.C. 154(b) by 104 days.

(21) Appl. No.: 13/121,857

(22) PCT Filed: Nov. 13, 2009

(86) PCT No.: PCT/JP2009/069392
§ 371 (c)(1),
(2), (4) Date: Mar. 30, 2011

(87) PCT Pub. No.: WO2010/061743
PCT Pub. Date: Jun. 3, 2010

(65) Prior Publication Data
US 2011/0178493 A1     Jul. 21, 2011

(30) Foreign Application Priority Data

Nov. 25, 2008 (JP) .................................. 2008-299994

(51) Int. Cl.
*A61M 5/00* (2006.01)
*A61M 39/00* (2006.01)
*A61J 1/22* (2006.01)

(52) U.S. Cl.
USPC ........... 604/406; 604/403; 604/404; 604/407; 604/411; 604/412; 604/413; 604/414; 604/415; 604/416

(58) Field of Classification Search
USPC .................. 604/406, 403, 404, 407, 409, 411, 604/412, 413, 414, 415, 416; 137/625.47
See application file for complete search history.

(56) References Cited

U.S. PATENT DOCUMENTS

| 4,397,335 | A | * | 8/1983 | Doblar et al. ............ 137/625.19 |
| 4,423,741 | A | | 1/1984 | Levy .............................. 600/581 |
| 4,534,758 | A | * | 8/1985 | Akers et al. ..................... 604/85 |
| 4,759,756 | A | | 7/1988 | Forman et al. ................ 604/413 |
| 4,972,876 | A | * | 11/1990 | Kabata et al. ............ 137/625.16 |
| 5,288,290 | A | * | 2/1994 | Brody .............................. 604/32 |
| 5,466,220 | A | * | 11/1995 | Brenneman ..................... 604/87 |
| 5,647,845 | A | * | 7/1997 | Haber et al. .................... 604/32 |
| 5,810,792 | A | | 9/1998 | Fangrow et al. .............. 604/533 |
| 5,871,110 | A | | 2/1999 | Grimard et al. |

(Continued)

FOREIGN PATENT DOCUMENTS

| CN | 101244297 | 8/2008 |
| JP | 56-95247 | 7/1981 |

(Continued)

*Primary Examiner* — Adam Marcetich
(74) *Attorney, Agent, or Firm* — Hamre, Schumann, Mueller & Larson, P.C.

(57) ABSTRACT

One end of a tubular portion (16) is sealed with a stopcock (5) that is fitted in the tubular portion (16). A first flow channel (33) and a second flow channel (36) are formed in the stopcock (5). A first hole (37), a second hole (43), a third hole (38), and a fourth hole (44) are formed in a connector main body (2). Switching between a setting that brings an inner space (16a) of the tubular portion (16) into communication with the first hole (37) via the first flow channel (33) and a setting that brings the inner space (16a) of the tubular portion (16) into communication with the second hole (43) via the first flow channel (33) and brings the third hole (38) into communication with the fourth hole (44) via the second flow channel (36) can be achieved by rotating the stopcock (5).

16 Claims, 22 Drawing Sheets

(56) References Cited

U.S. PATENT DOCUMENTS

| | | |
|---|---|---|
| 6,193,675 B1 | 2/2001 | Kraus et al. .................... 600/576 |
| 6,221,041 B1* | 4/2001 | Russo ............................. 604/82 |
| 2001/0029360 A1* | 10/2001 | Miyoshi et al. ............... 604/411 |
| 2002/0017328 A1* | 2/2002 | Loo .......................... 137/625.47 |
| 2002/0095121 A1 | 7/2002 | Norton et al. ................. 604/187 |
| 2002/0189712 A1 | 12/2002 | Safabash ....................... 141/329 |
| 2003/0023226 A1 | 1/2003 | Lopez |
| 2003/0153895 A1 | 8/2003 | Leinsing |
| 2004/0225274 A1 | 11/2004 | Jansen et al. |
| 2004/0249341 A1* | 12/2004 | Newbrough et al. ........... 604/87 |
| 2005/0033260 A1* | 2/2005 | Kubo et al. ................... 604/411 |
| 2007/0079894 A1* | 4/2007 | Kraus et al. ................... 141/319 |
| 2007/0088313 A1 | 4/2007 | Zinger et al. ................. 604/403 |
| 2007/0244447 A1 | 10/2007 | Capitaine et al. ............. 604/256 |
| 2007/0287953 A1* | 12/2007 | Ziv et al. ......................... 604/31 |
| 2008/0269680 A1 | 10/2008 | Ibranyan et al. |
| 2009/0326506 A1 | 12/2009 | Hasegawa et al. |
| 2010/0286606 A1 | 11/2010 | Ding |
| 2011/0175347 A1 | 7/2011 | Okiyama |

FOREIGN PATENT DOCUMENTS

| | | |
|---|---|---|
| JP | 62-189072 | 8/1987 |
| JP | 10-118158 | 5/1998 |
| JP | 2001-190689 | 7/2001 |
| JP | 2002-238979 | 8/2002 |
| JP | 2007-215775 | 8/2007 |
| WO | 2005/041846 | 5/2005 |
| WO | 2007/148708 | 12/2007 |

* cited by examiner

CONNECTOR

TECHNICAL FIELD

The present invention relates to a connector that is capable of switching flow channels, and particularly relates to a medical connector for transferring a liquid between, for example, a drug solution bag and a vial.

BACKGROUND ART

Drugs such as anticancer agents may be stored in the form of powder for storage stability and may be dissolved before use. In this case, a solvent is injected into a vial containing a drug, and a drug solution generated by dissolving the drug in the solvent is injected into a drug solution bag. Then, the drug solution in the drug solution bag is administered into the body via a tube attached to the drug solution bag. For example, the below-listed Patent Documents 1 and 2 propose devices for injecting a drug solution in the vial into the drug solution bag.

Patent Document 1 proposes that a mouth portion of a container (a vial) containing a drug is pierced with one end of a double-ended needle and a mouth portion of a container (a drug solution bag) containing a diluent is pierced with the other end of the double-ended needle, and in this state, a drug solution generated by dissolution in the drug-containing container is injected into the diluent-containing container. At this time, air is fed into the drug-containing container by supplying air with a syringe (an air supply means and drawing means) connected to the double-ended needle so that the drug solution is transferred quickly from the drug-containing container into the diluent-containing container.

Patent Document 2 proposes that a stopper of a glass bottle (a vial) is pierced with a bottle needle formed in a transfer device and a stopper of an empty bag (a drug solution bag) is pierced with a hollow needle, and in this state, a fluid contained in the glass bottle is transferred into the empty bag. At this time, external air is fed into the glass bottle by operating a pump provided in the transfer device so that the drug solution in the glass bottle can be transferred smoothly into the empty bag.

CITATION LIST

Patent Documents

Patent Document 1: JP 2002-238979A
Patent Document 2: JP S56-95247U

DISCLOSURE OF INVENTION

Problem to be Solved by the Invention

However, the amount of drug solution to be injected into the drug solution bag differs from patient to patient, and there have been cases where it is necessary to adjust the amount of drug solution to be injected so as to be appropriate for individual patients. According to the devices proposed in Patent Documents 1 and 2, it was difficult to adjust the amount of drug solution to be injected, even though it was possible to transfer the drug solution from the vial into the drug solution bag quickly or smoothly. The reason for this is that with the devices proposed in Patent Documents 1 and 2, it is air, rather than the drug solution, that is fed by operation of the syringe or the pump. That is to say, although it is possible to accelerate transfer of the drug solution into the drug solution bag by feeding in air, the amount of drug solution to be injected varies depending on the pressure in the drug solution bag, and it was difficult to adjust the amount of drug solution to be injected with precision even when the amount of operation of the syringe or the pump is adjusted.

The present invention has been made to solve conventional problems such as those described above, and it is an object thereof to provide a connector that is capable of injecting a required amount of drug solution into a drug solution bag with precision.

Means for Solving Problem

In order to achieve the above-described object, a connector of the present invention is a connector including a connector main body provided with a tubular portion and a stopcock that is fitted in the tubular portion so as to be rotatable around an axis of the tubular portion, wherein one end of the tubular portion is sealed with the stopcock that is fitted in the tubular portion; a first flow channel and a second flow channel are formed in the stopcock; a first hole, a second hole, a third hole, and a fourth hole are formed in the connector main body; the first, the second, the third, and the fourth holes are holes that bring an inner space of the tubular portion into communication with an external space of the connector main body; and switching between a setting that brings the inner space of the tubular portion into communication with the first hole via the first flow channel and a setting that brings the inner space of the tubular portion into communication with the second hole via the first flow channel and brings the third hole into communication with the fourth hole via the second flow channel can be achieved by rotating the stopcock.

Effects of the Invention

With the connector of the present invention, it is possible to inject a required amount of drug solution into a drug solution bag with precision.

DESCRIPTION OF THE INVENTION

Figure 1:
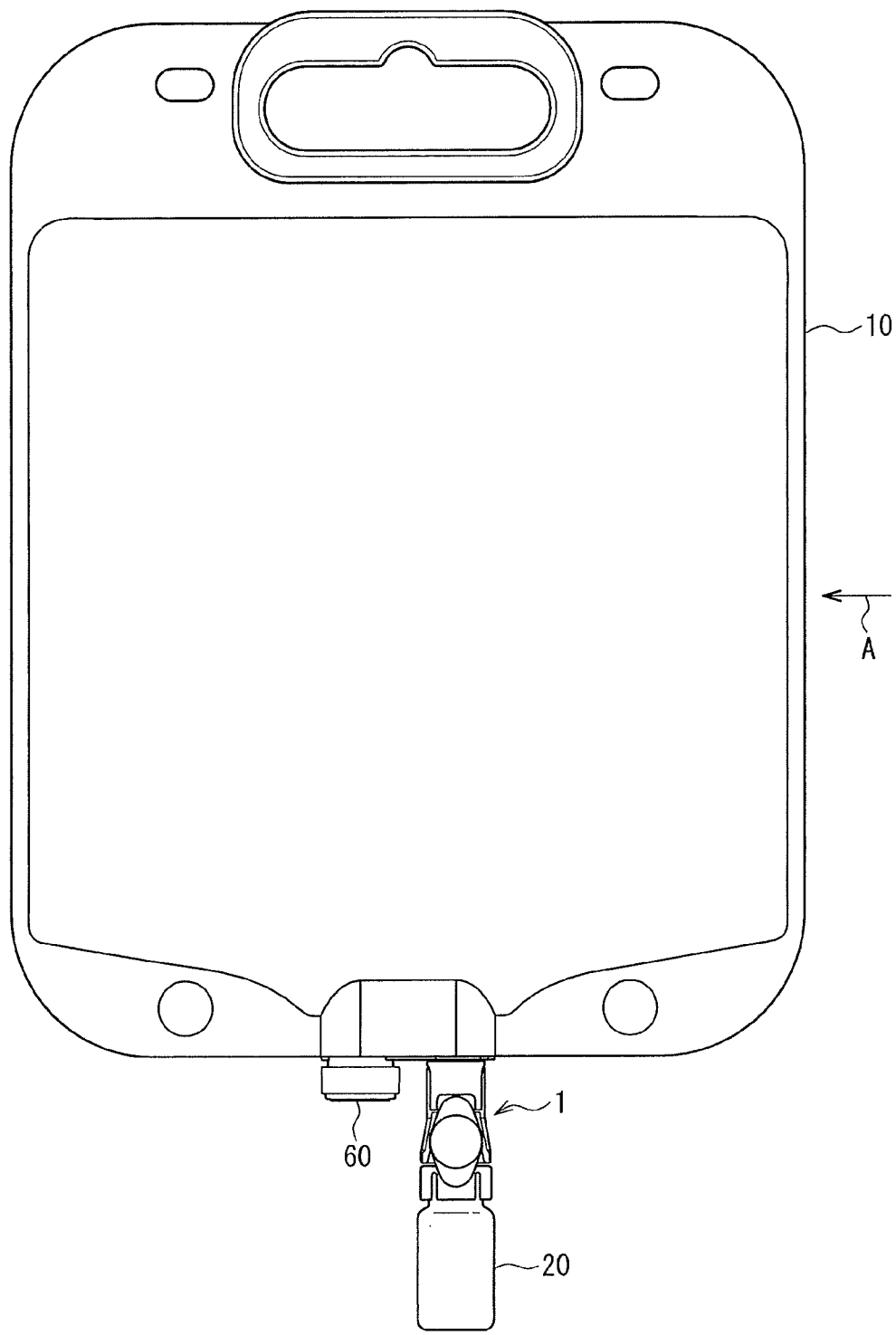
FIG. 1 is a diagram showing an example of use of a connector 1 according to Embodiment 1 of the present invention.

According to the present invention, when a syringe, a drug solution bag, and a vial are connected to the connector, it is possible to transfer a liquid between the vial and the drug solution bag via the syringe by switching between the flow channel settings within the connector, and it is also possible to adjust accurately the amount of the liquid to be transferred. Thus, a required amount of drug solution can be injected into the drug solution bag with precision.

In the connector of the present invention, it is preferable that a first connecting portion and a second connecting portion are provided in the connector main body; connecting ports are formed in the first and the second connecting portions; the first and the third holes are in communication with a space in the first connecting portion; and the second and the fourth holes are in communication with a space on the connecting port side of the second connecting portion. This configuration facilitates connection of the connector to the drug solution bag and the vial.

Moreover, it is preferable that the first flow channel is a recess formed in a side face of the stopcock, the recess extending to a leading end face of the stopcock and forming a notch in the leading end face of the stopcock. With this configuration, a flow channel can be formed between the recess and an inner circumferential surface of the tubular portion.

Moreover, it is preferable that both ends of the second flow channel are located at mutually different positions in an axial direction and in a circumferential direction of the stopcock. With this configuration, the state in which the ends of the second flow channel respectively communicate with the third hole and the fourth hole can be changed to the state in which the second flow channel is not interposed between the third hole and the fourth hole by rotating the stopcock. Thus, it is possible to switch between the state in which transfer between the third hole and the fourth hole is possible and the state in which transfer between the third hole and the fourth hole is not possible by rotating the stopcock.

Moreover, it is preferable that the second flow channel is a recess formed in a side face of the stopcock so as to have a spiral shape.

Moreover, it is preferable that the first flow channel is a hole that brings an opening formed on a leading end side of the stopcock into communication with an opening formed in a side face of the stopcock.

Moreover, it is preferable that the second flow channel is a penetrating flow channel that passes through the stopcock in a radial direction of the stopcock.

Moreover, it is preferable that a check valve is provided in at least one of the third hole and the fourth hole, and when the stopcock is set to the setting that brings the third hole into communication with the fourth hole via the second flow channel, liquid transfer through the third hole and the fourth hole is stopped by the check valve. With this configuration, when the syringe, the drug solution bag, and the vial are connected to the connector, it is possible to prevent a liquid from being transferred between the drug solution bag and the vial without passing through the syringe even in the case where the syringe is erroneously operated.

Moreover, it is preferable that the first connecting portion includes a lever lock that is integral with the connecting port formed in the first connecting portion. This configuration facilitates attachment and detachment of the first connecting portion.

Moreover, it is preferable that the second connecting portion has a protrusion protruding from an inner circumferential surface of the connecting port formed in the second connecting portion. With this configuration, it is possible to prevent the second connecting portion from falling off.

Moreover, it is preferable that the first connecting portion has a portion covered with a shield that can open and close by extension and retraction. With this configuration, leakage of the drug solution from the first connecting portion can be prevented even after the first connecting portion has been detached from the drug solution bag. Therefore, if the vial is disposed of in a state in which the second connecting portion and the vial remain in the connected state, leakage of the drug in the vial will be prevented.

Moreover, it is preferable that a graduated syringe including a cylinder and a movable piston is formed integrally on the other end side of the tubular portion. This configuration facilitates assembly of the connector prior to operation. Moreover, erroneous detachment of the syringe and resulting opening of the other end of the tubular portion can be prevented.

Moreover, it is preferable that a lever extended from the stopcock is formed on the stopcock, and the lever is disposed in such a manner that when the stopcock is set to the setting that brings the inner space of the tubular portion into communication with the first hole via the first flow channel, a leading end of the extended lever points to an external space side communicating with the first hole, and when the stopcock is set to the setting that brings the inner space of the tubular portion into communication with the second hole via the first flow channel, the leading end of the extended lever points to an external space side communicating with the second hole. With this configuration, it is possible to determine the status of the flow channel setting within the connector from the orientation of the lever.

Moreover, it is preferable that a lever extended from the stopcock is formed on the stopcock, and the lever is disposed in such a manner that when the stopcock is set to the setting that brings the inner space of the tubular portion into communication with the first hole via the first flow channel, a leading end of the extended lever points to an external space side communicating with the second hole, and when the stopcock is set to the setting that brings the inner space of the tubular portion into communication with the second hole via the first flow channel, the leading end of the extended lever points to an external space side communicating with the first hole. With this configuration, it is possible to determine the status of the flow channel setting within the connector from the orientation of the lever.

Moreover, it is preferable that a hydrophobic filter is provided in at least one of the third hole, the penetrating flow channel, and the fourth hole. With this configuration, when the syringe, the drug solution bag, and the vial are connected to the connector, liquid transfer between the drug solution bag and the vial via the third hole, the penetrating flow channel, and the fourth hole reliably can be prevented. This also renders accurate adjustment of the amount of liquid to be transferred between the vial and the drug solution bag via the syringe more reliable.

Hereinafter, embodiments of the present invention will be described with reference to the drawings.

Embodiment 1

FIG. 1 is a diagram showing an example of use of a connector 1 according to Embodiment 1 of the present invention. In the example in this diagram, a drug solution bag 10 and a vial 20 are connected to each other via the connector 1. The drug solution bag 10 is formed by shaping a soft resin sheet into a pouch-like shape. The drug solution bag 10 can be formed by, for example, superposing two resin sheets over each other and joining their peripheral edge portions together by heat welding or the like. The vial 20 is a container containing a drug and is, for example, a glass bottle whose opening is sealed with a rubber stopper and a cap.

Figure 2:
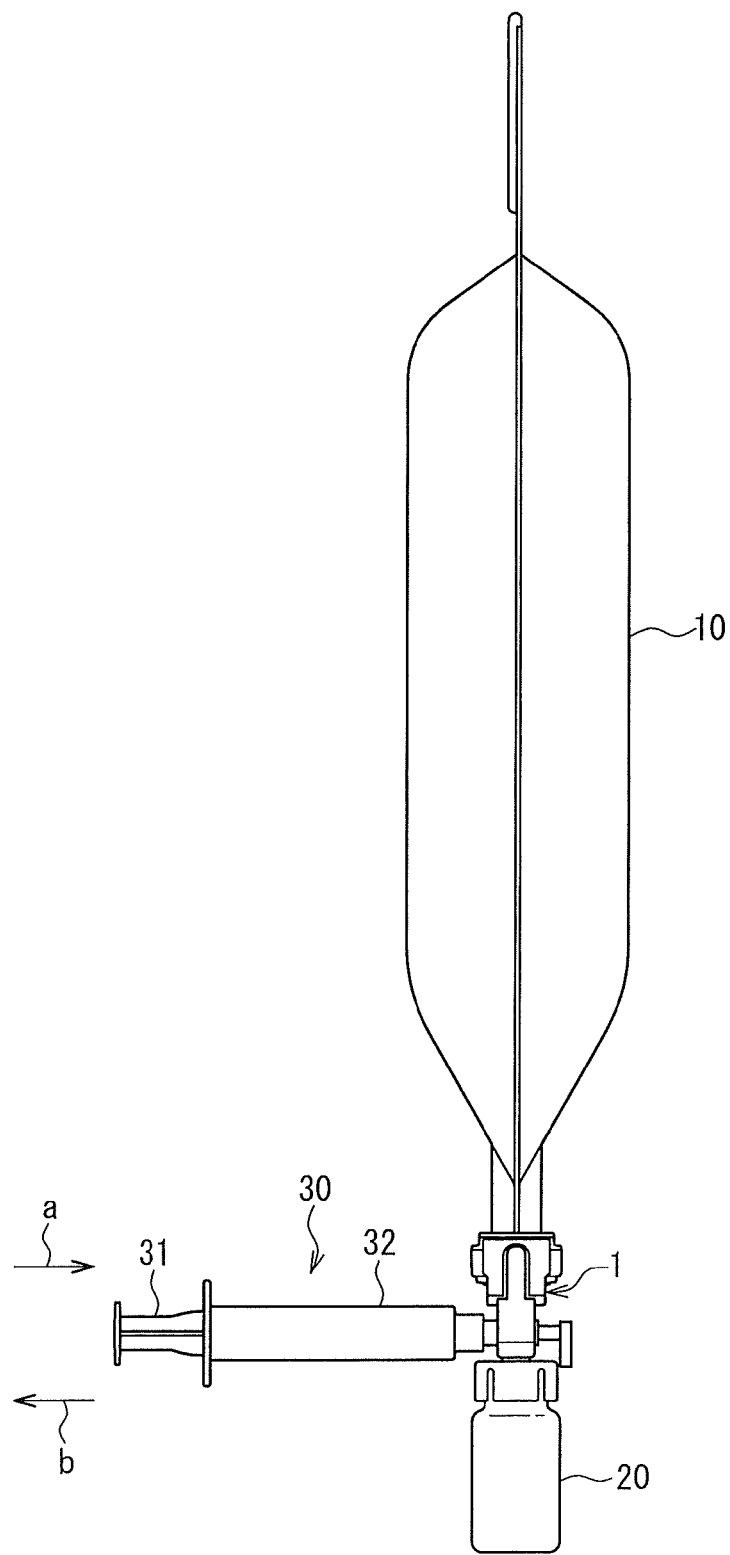
FIG. 2 is a diagram showing the example in FIG. 1 as seen from the direction of arrow A.

FIG. 2 shows the example in FIG. 1 as seen from the direction of arrow A. A syringe 30 is attached to the connector 1. The syringe 30 includes a hollow cylindrical cylinder 32 and a movable piston 31. Pushing the piston 31 in the direction of arrow "a" can cause a liquid in the cylinder 32 to be ejected from a leading end of the cylinder 32. On the other hand, pulling the piston 31 in the direction of arrow "b" can cause a liquid to be drawn into the cylinder 32.

Figure 3:
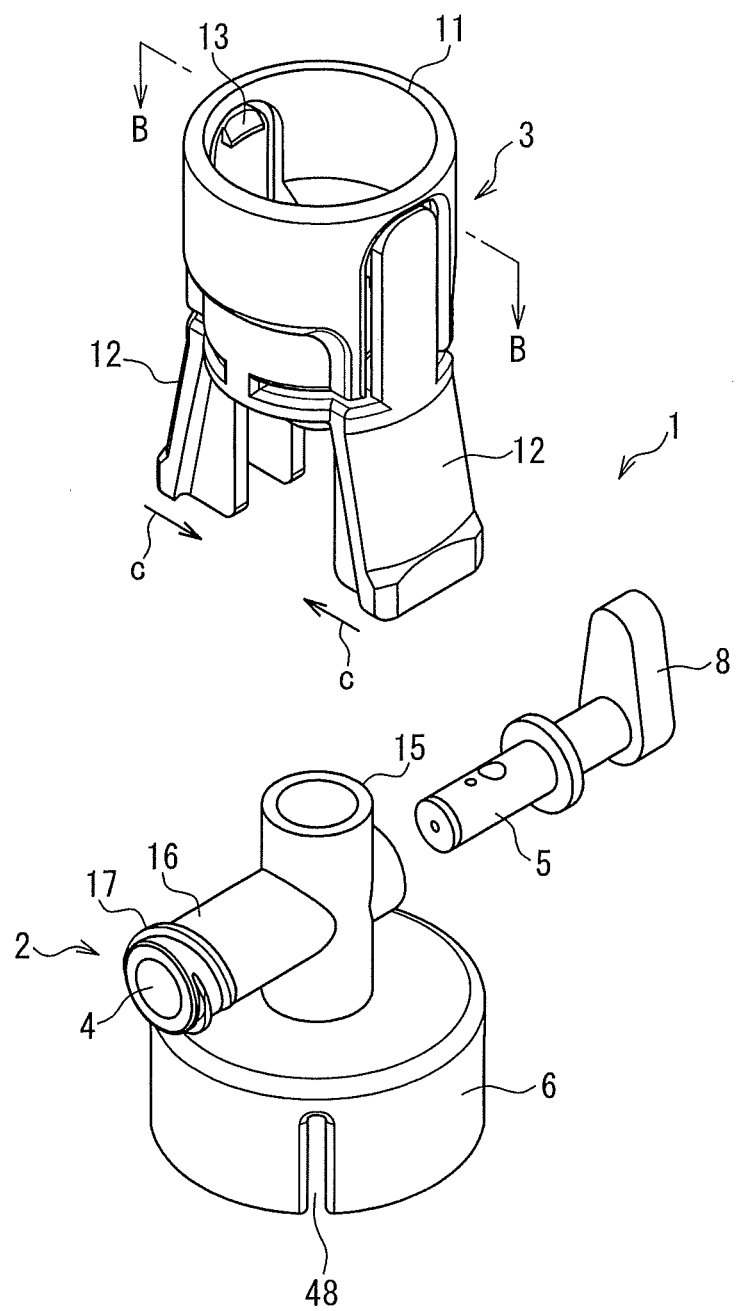
FIG. 3 is an exploded perspective view of the connector 1 according to Embodiment 1 of the present invention.

FIG. 3 is an exploded perspective view of the connector 1. As shown in FIG. 3, the connector 1 can be disassembled into a connector main body 2, a first connecting portion 3, and a stopcock 5. The connector main body 2 is integral with a second connecting portion 6.

It should be noted that in the following description, the portion denoted by reference numeral 2 in FIG. 3 is referred to as the connector main body 2. However, this is for the sake of convenience, and the connector main body 2 and the first connecting portion 3 connected thereto may be collectively regarded as the connector main body 2.

The first connecting portion 3 is integrally provided with a hollow cylindrical connecting port 11 and lever locks 12. The first connecting portion 3 is a connector for connecting the connector 1 to the drug solution bag 10 (FIG. 1). During connection to the drug solution bag 10, a hollow cylindrical port portion 41 (FIG. 10) fixed to the drug solution bag 10 is inserted into the connecting port 11.

At this time, while lower portions of the lever locks 12 are bent in the direction of arrow "c", claw portions 13 of the lever locks 12 engage an end face 41a (FIGS. 10 and 11) of the port portion 41. Details of the connection of the first connecting portion 3 to the drug solution bag 10 will be described later with reference to FIGS. 10 and 11.

The connector main body 2 includes an axial tubular portion 15 and a horizontal tubular portion 16 intersecting with each other. A thread 17 is formed on the horizontal tubular portion 16 for the purpose of screwing to the syringe 30 (FIG. 2). The cylindrical stopcock 5 is inserted into the horizontal tubular portion 16. When a lever 8 is rotated, the stopcock 5 rotates around an axis of the horizontal tubular portion 16.

The connector 1, in a connected state as shown in FIG. 2, allows liquid transfer between the drug solution bag 10 and the vial 20 via the syringe 30. By rotating the stopcock 5 (FIG. 3), it is possible to switch between a flow channel setting that allows liquid transfer between the drug solution bag 10 and the syringe 30 and a flow channel setting that allows liquid transfer between the vial 20 and the syringe 30. Details of the switching will be described later with reference to FIGS. 6 to 9.

As described above, in FIG. 3, the connector main body 2 is integral with the second connecting portion 6. The second connecting portion 6 is for connecting the connector main body 2 to the vial 20. A hollow cylindrical connecting port 49 (FIG. 4) is formed in the second connecting portion 6. During connection of the second connecting portion 6 to the vial 20, a cap portion of the vial 20 is fitted into the connecting port 49 of the second connecting portion 6. Details of this connection will be described later with reference to FIGS. 12 and 13.

Figure 4:
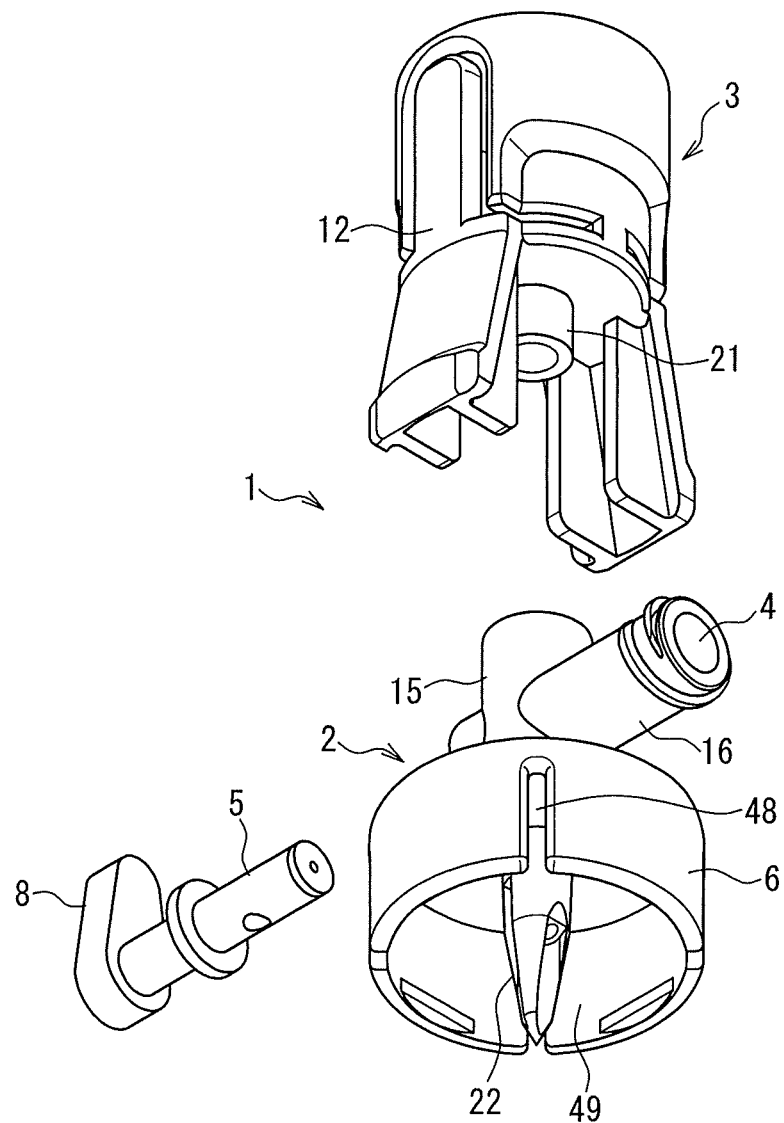
FIG. 4 is an exploded perspective view of the connector 1 in FIG. 3 as seen from a different angle from that of FIG. 3.

FIG. 4 is an exploded perspective view of the connector 1 as seen from a different angle from that of FIG. 3. FIG. 4 shows a back side of the first connecting portion 3 and the connector main body 2. A connecting tubular portion 21 is formed on the back side of the first connecting portion 3. The first connecting portion 3 can be connected to the connector main body 2 by fitting an outer circumferential surface of this connecting tubular portion 21 to an inner circumferential surface (FIG. 3) of the axial tubular portion 15 of the connector main body 2.

A needle-like portion 22 is formed on the back side of the connector main body 2. The needle-like portion 22 has a sharp tip, and a rubber stopper 23 (FIG. 5) of the vial 20 can be pierced with the needle-like portion 22.

Figure 5:
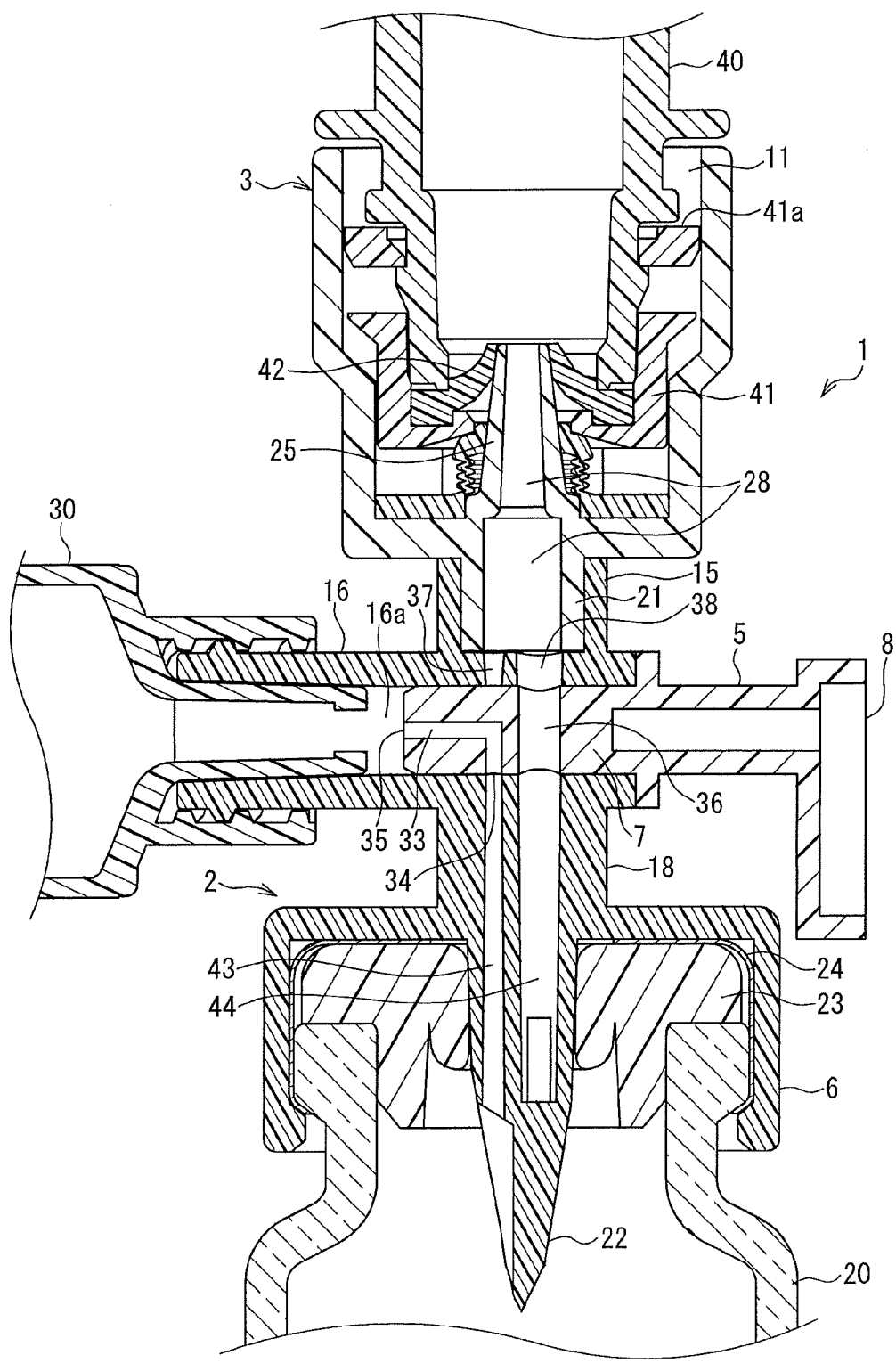
FIG. 5 is a cross-sectional view of the connector 1 according to Embodiment 1 of the present invention.
Figure 10:
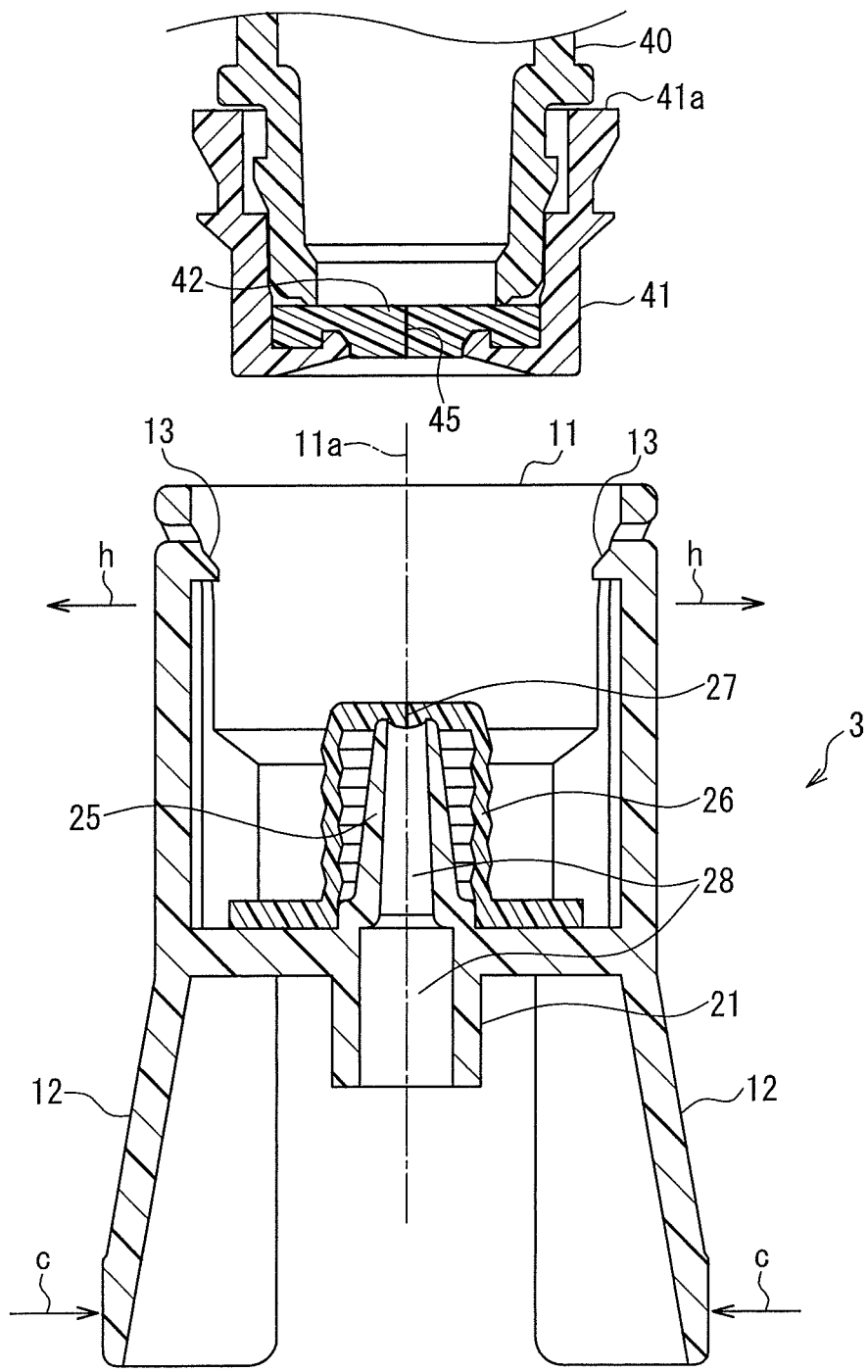
FIG. 10 is a cross-sectional view showing a state before a first connecting portion 3 according to an embodiment of the present invention is connected to the drug solution bag 10.
Figure 11:
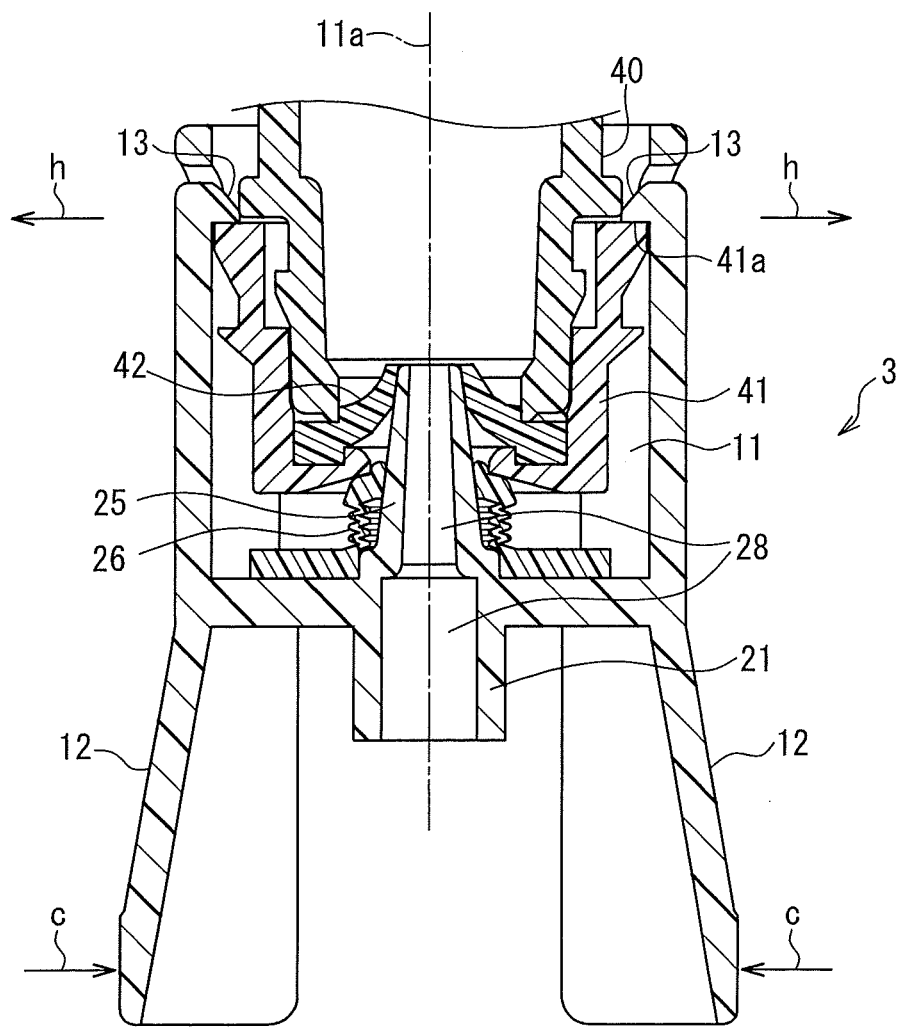
FIG. 11 is a cross-sectional view showing a state in which the first connecting portion 3 according to the embodiment of the present invention has been connected to a port portion 41.

FIG. 5 shows a cross-sectional view of the connector 1. This cross-sectional view corresponds to a vertical cross-sectional view of the connector 1 and its peripheral portions shown in FIG. 2. The port portion 41 is attached to a leading end portion of a connecting port 40 attached to the drug solution bag 10. The port portion 41 is inserted in the connecting port 11 of the first connecting portion 3. Although not shown in this cross-sectional view, the claw portions 13 (FIG. 3) of the lever locks 12 that are integral with the first connecting portion 3 are engaged with the end face 41a of the port portion 41 to connect the first connecting portion 3 to the port portion 41 (FIG. 11). As described above, details of this connection will be described later with reference to FIGS. 10 and 11.

The first connecting portion 3 has an upright tubular portion 25 formed in a central portion of the connecting port 11. A leading end portion of the upright tubular portion 25 pushes up a septum (a partition) 42 attached to the port portion 41. The septum 42 is made of a soft material, and a slit is formed therein. In the state shown in FIG. 5, the leading end portion of the upright tubular portion 25 forces the slit of the septum 42 open by pushing up the septum 42. Thus, an inner space of the connecting port 40 is in communication with inner spaces 28 of the upright tubular portion 25 and the connecting tubular portion 21.

The outer circumferential surface of the connecting tubular portion 21 of the first connecting portion 3 is fitted to the inner circumferential surface of the axial tubular portion 15 of the connector main body 2. Thus, the first connecting portion 3 is connected to the connector main body 2.

The stopcock 5 is inserted in the horizontal tubular portion 16 of the connector main body 2. One end of the horizontal tubular portion 16 is sealed with the stopcock 5, and an open portion 4 (FIGS. 3 and 4) is formed at the other end of the horizontal tubular portion 16. A first flow channel 33, which is an L-shaped flow channel, is formed in the stopcock 5, and an opening 35 formed on a leading end side of the stopcock 5 is in communication with an opening 34 formed in a side face of the stopcock 5. Furthermore, a second flow channel 36, which is a penetrating flow channel that passes through the stopcock 5 in a radial direction thereof, is formed in the stopcock 5.

It should be noted that in the present embodiment, an example in which the first flow channel 33 is a flow channel having an L shape has been described. However, all that is required is that the opening 34 and the opening 35 are in communication with each other, and the shape of the flow channel is not limited to an L shape.

A first hole 37 and a second hole 43 are formed in the connector main body 2. These two holes are both holes that bring an inner space 16a of the horizontal tubular portion 16 into communication with an external space of the connector main body 2. The first hole 37 passes through a side wall portion of the horizontal tubular portion 16, and the second hole 43 passes through a base portion 18 and the needle-like portion 22.

Furthermore, a third hole 38 and a fourth hole 44 are formed in the connector main body 2. These two holes are also holes that bring the inner space 16a of the horizontal tubular portion 16 into communication with the external space of the connector main body 2 as is the case with the first hole 37 and the second hole 43. The third hole 38 passes through the side wall portion of the horizontal tubular portion 16, and the fourth hole 44 passes through the base portion 18 and the needle-like portion 22.

When the lever 8 is rotated, the stopcock 5 rotates around the axis of the horizontal tubular portion 16. Due to this rotation, the opening 34 rotationally moves in an outer circumferential direction of the stopcock 5.

In the state shown in FIG. 5, the first flow channel 33 communicates with the second hole 43. The second flow channel 36 communicates with the third hole 38 and the fourth hole 44. By rotating the lever 8 from this state, the first flow channel 33 can be set to a state in which it communicates with the first hole 37.

That is to say, by rotating the lever 8, it is possible to switch between a setting that brings the first flow channel 33 into communication with the second hole 43 and a setting that brings the first flow channel 33 into communication with the first hole 37. This switching between the settings can be used to transfer a solvent in the drug solution bag 10 into the vial 20 to generate a drug solution by dissolving a drug in powder form contained in the vial 20 in the solvent, and afterward to inject this drug solution into the drug solution bag 10. Details of this will be described later with reference to FIGS. 6 to 9.

The opening of the vial 20 is sealed with the rubber stopper 23 and a cap 24. The rubber stopper 23 is press-fitted in the opening of the vial 20. The cap 24 is formed by, for example, processing a sheet metal, and covers the opening of the vial 20. As shown in FIG. 5, the vial 20 and the connector main body 2 are connected to each other by the second connecting portion 6. Details of this connection will be described later with reference to FIGS. 12 and 13.

Hereinafter, an operating procedure during injection of the drug in the vial 20 into the drug solution bag 10 will be described with reference to FIGS. 6 to 9. In the drawings described below, the connecting port 40, the port portion 41, the syringe 30, and the vial 20 in FIG. 5 are shown simplified in chain double-dashed lines for clarity of illustration.

Figure 6:
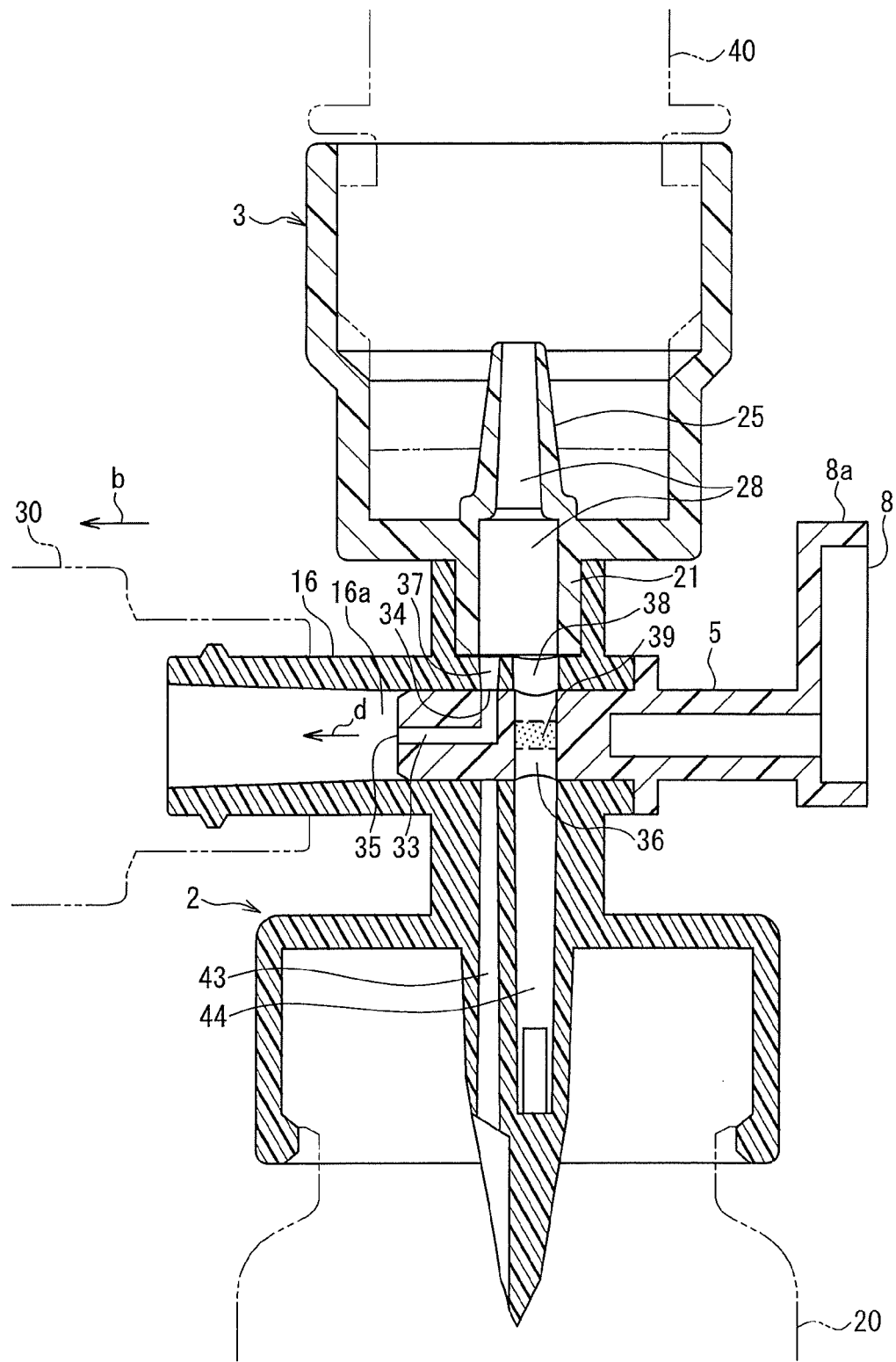
FIG. 6 is a cross-sectional view showing a state in which a solvent in a drug solution bag 10 is drawn into a syringe 30 from a connecting port 40, according to Embodiment 1 of the present invention.

FIG. 6 is a cross-sectional view showing a state in which the solvent in the drug solution bag 10 is drawn into the syringe 30 from the connecting port 40. In FIG. 6, the stopcock 5 is in the setting that brings the opening 34 of the first flow channel 33 into communication with the first hole 37. Accordingly, the solvent in the drug solution bag 10 can flow to the inner space 16a of the horizontal tubular portion 16 through the connecting port 40, the inner spaces 28 of the upright tubular portion 25 and the connecting tubular portion 21, the first hole 37, the first flow channel 33, and the opening 35.

When the stopcock 5 is in the setting shown in FIG. 6, pulling the piston 31 (FIG. 2) of the syringe 30 in the direction of arrow "b" can cause the solvent in the drug solution bag 10 to be drawn into the inner space 16a of the horizontal tubular portion 16 and further into the syringe 30 (the direction of arrow "d").

In this case, an amount of the solvent corresponding to the amount by which the piston 31 is pulled is drawn into the syringe 30. Thus, the amount of the solvent to be drawn into the syringe 30 can be adjusted by adjusting the amount by which the piston 31 is pulled while looking at a scale on the cylinder 32. That is to say, a required amount of the solvent can be drawn into the syringe 30 with precision.

In the state shown in FIG. 6, when the pressure in the vial 20 is set to positive pressure, it is possible to prevent the solvent in the drug solution bag 10 from going into the vial 20 through the third hole 38, the second flow channel 36, and the fourth hole 44. To ensure this, a hydrophobic filter can be provided in at least one of the third hole 38, the second flow channel 36, and the fourth hole 44. FIG. 6 shows an example in which a hydrophobic filter 39 is provided in the second flow channel 36.

The hydrophobic filter has air permeability and allows air, but not liquid, to pass through. Therefore, even when the pressure in the vial 20 is not positive, it is possible to prevent the solvent in the drug solution bag 10 from directly flowing into the vial 20.

Figure 7:
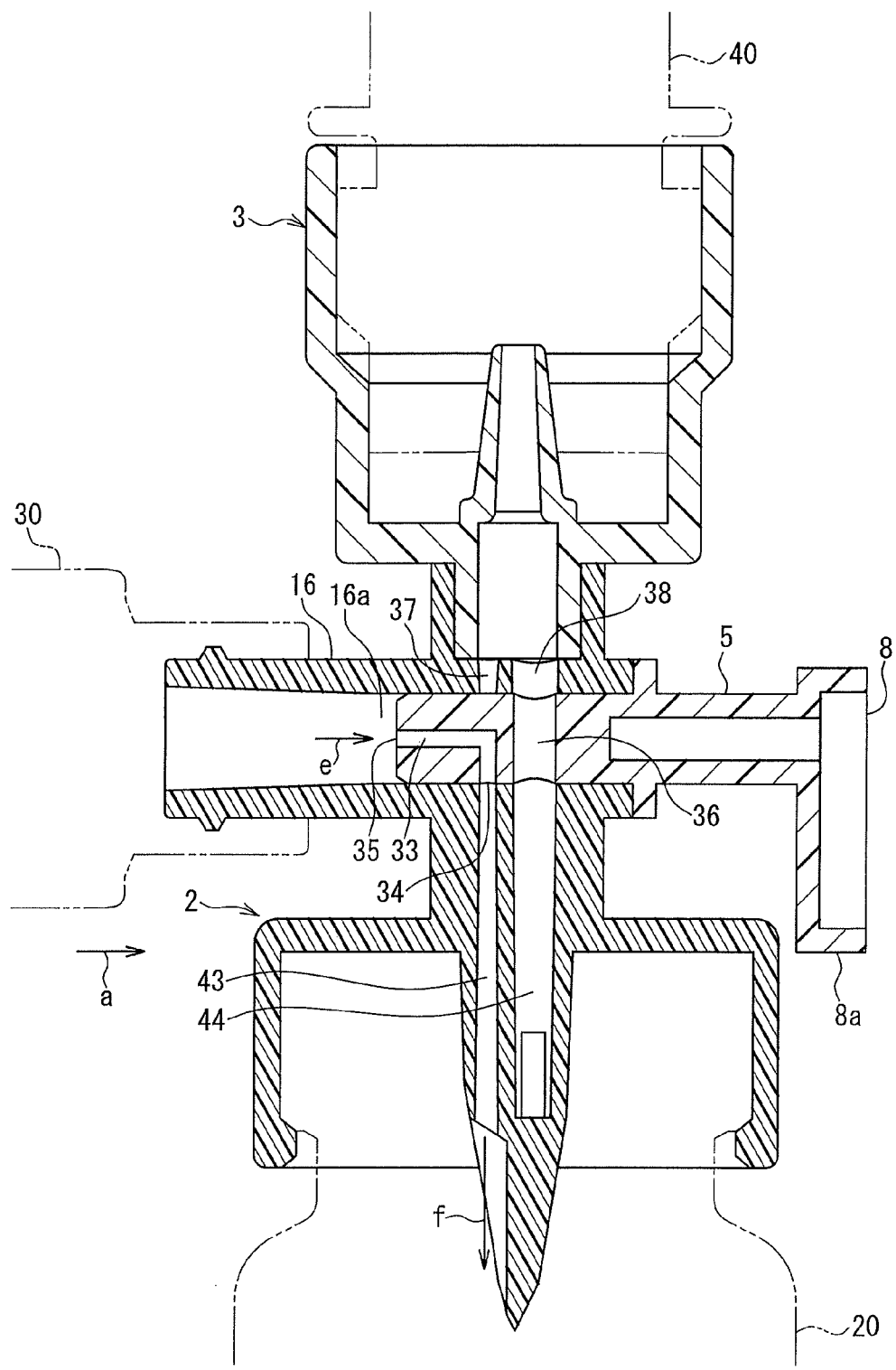
FIG. 7 is a cross-sectional view showing a state in which the solvent that has been drawn into the syringe 30 is injected into a vial 20, according to Embodiment 1 of the present invention.

FIG. 7 is a cross-sectional view showing a state in which the solvent that has been drawn into the syringe 30 is injected into the vial 20. The setting of the stopcock 5 shown in FIG. 7 is different from that in FIG. 6. In FIG. 7, the stopcock 5 has been rotated by rotating the lever 8 from the state shown in FIG. 6. In FIG. 6, the opening 34 of the stopcock 5 is positioned on the upper side, whereas in FIG. 7, the opening 34 is positioned on the lower side. That is to say, in FIG. 7, the stopcock 5 is in the setting that brings the first flow channel 33 into communication with the second hole 43.

In the state shown in FIG. 7, when the piston 31 (FIG. 2) of the syringe 30 is pushed in the direction of arrow "a", the solvent in the syringe 30 is expelled into the inner space 16a of the horizontal tubular portion 16. The solvent that has reached the inner space 16a flows in the direction of arrow "e" and passes through the first flow channel 33 and the second hole 43 to be injected into the vial 20 as indicated by arrow "f".

In this case, an amount of the solvent corresponding to the amount by which the piston 31 is pushed flows out of the syringe 30. Thus, the amount of the solvent to be caused to flow out of the syringe 30 can be adjusted by adjusting the amount by which the piston 31 is pushed while looking at the scale on the cylinder 32. That is to say, a required amount of the solvent can be injected into the vial 20 with precision.

During injection of the solvent into the vial 20, air in the vial 20 passes up through the fourth hole 44 and flows into the drug solution bag 10 via the connecting port 40. This also applies to the case where a hydrophobic filter is provided in the flow channel from the fourth hole 44 to the third hole 38 as described above. That is to say, the air permeability of the hydrophobic filter allows air in the vial 20 to flow into the drug solution bag 10.

Once the solvent is injected into the vial 20, the drug in powder form contained in the vial 20 is dissolved in the solvent. It is possible to accelerate the dissolution by shaking the vial 20.

Figure 8:
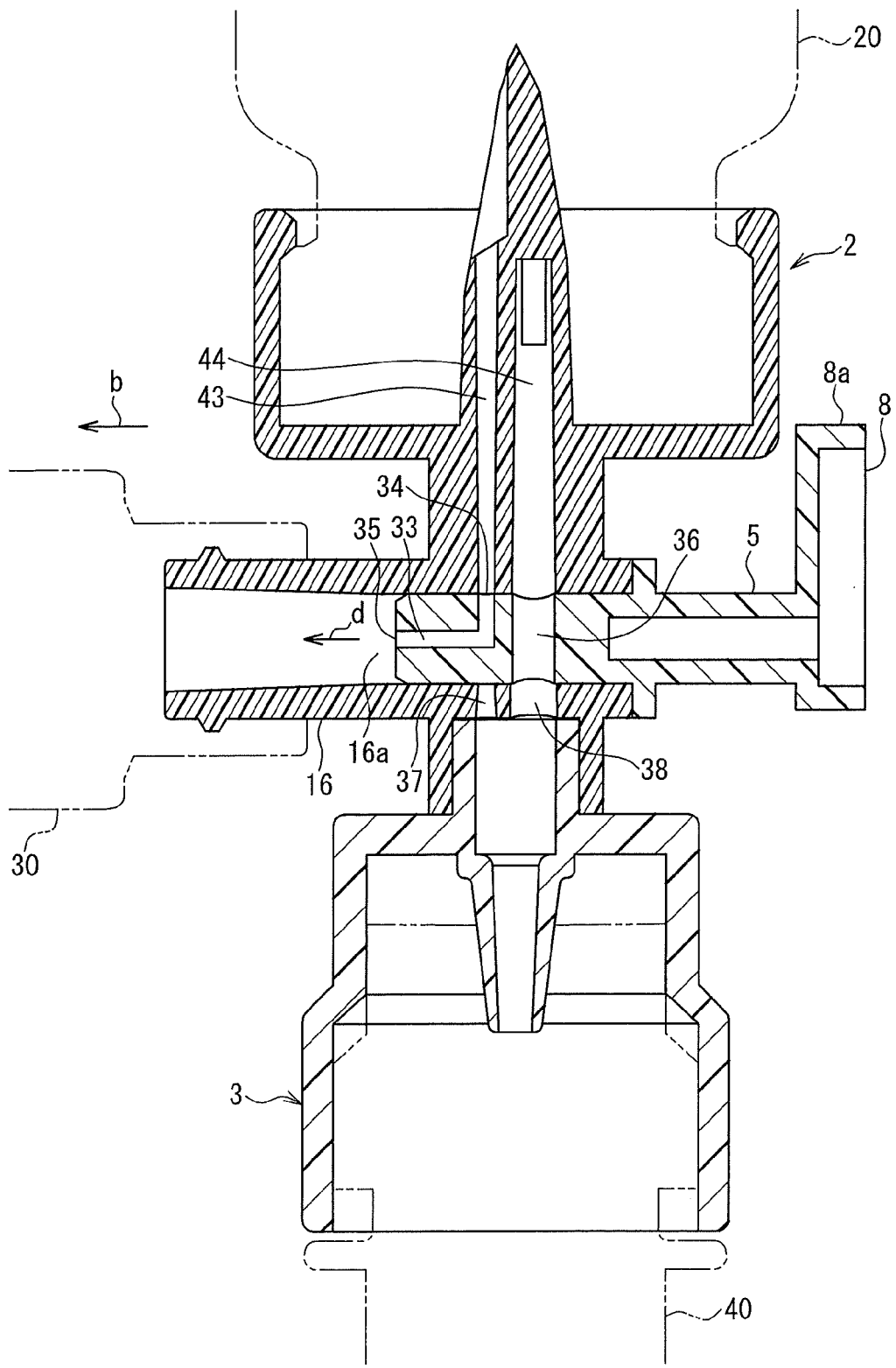
FIG. 8 is a cross-sectional view showing a state in which a drug solution that has been generated within the vial 20 is drawn into the syringe 30, according to Embodiment 1 of the present invention.

FIG. 8 is a cross-sectional view showing a state in which the drug solution that has been generated within the vial 20 by dissolving the drug in powder form is drawn into the syringe 30. In FIG. 8, the vertical relationship between the connecting port 40 of the drug solution bag 10 and the vial 20 is inverted with respect to that shown in FIGS. 6 and 7. That is to say, in FIGS. 6 and 7, the vial 20 is positioned on the lower side, whereas in FIG. 8, the vial 20 is positioned on the upper side. In this arrangement, the drug solution in the vial 20 can flow to the inner space 16a of the horizontal tubular portion 16 through the second hole 43 and the first flow channel 33.

As described above, when a hydrophobic filter is provided in the flow channel from the fourth hole 44 to the third hole 38, it is possible to prevent the drug solution in the vial 20 from directly flowing to the drug solution bag 10 via the connecting port 40 because the drug solution in the vial 20 does not pass through the hydrophobic filter.

When the stopcock 5 is in the setting shown in FIG. 8, pulling the piston 31 (FIG. 2) of the syringe 30 in the direction of arrow "b" can cause the drug solution in the vial 20 to be drawn into the inner space 16a of the horizontal tubular portion 16 and further into the syringe 30 (the direction of arrow "d").

In this case, an amount of the drug solution corresponding to the amount by which the piston 31 is pulled is drawn into the syringe 30. Therefore, the amount of the drug solution to be drawn into the syringe 30 can be adjusted by adjusting the amount by which the piston 31 is pulled while looking at the scale on the cylinder 32. That is to say, a required amount of the drug solution can be drawn into the syringe 30 with precision.

Figure 9:
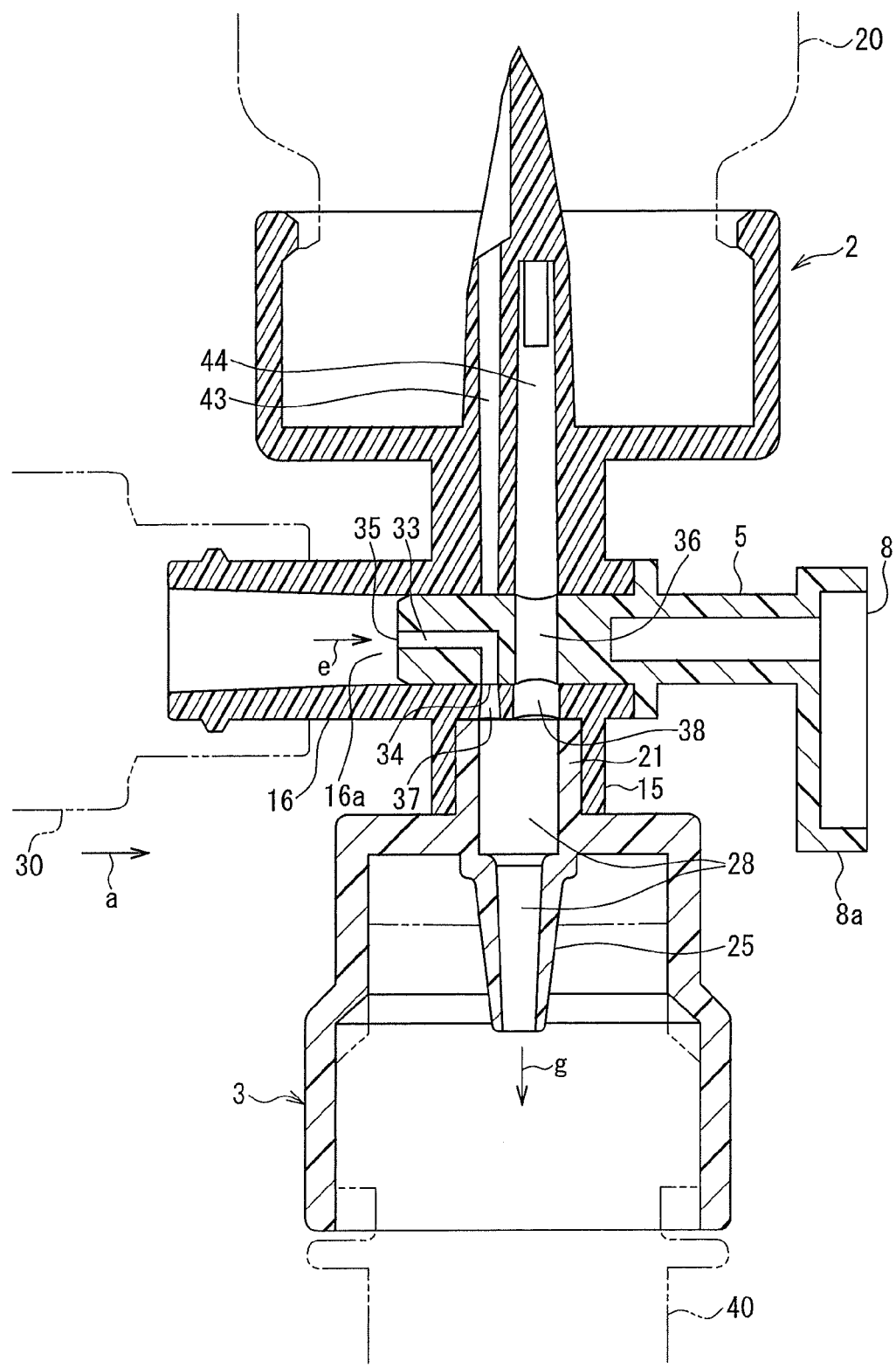
FIG. 9 is a cross-sectional view showing a state in which the drug solution that has been drawn into the syringe 30 is injected into the drug solution bag 10, according to Embodiment 1 of the present invention.

FIG. 9 is a cross-sectional view showing a state in which the drug solution that has been drawn into the syringe 30 is injected into the drug solution bag 10. In FIG. 9, the vertical relationship between the drug solution bag 10 and the vial 20 is the same as that in the state shown in FIG. 8, and the vial 20 remains positioned on the upper side. In FIG. 9, the setting of the stopcock 5 is different from that in FIG. 8. In FIG. 9, the stopcock 5 has been rotated by rotating the lever 8 from the state shown in FIG. 8. In FIG. 8, the opening 34 of the stopcock 5 is positioned on the upper side, whereas in FIG. 9, the opening 34 is positioned on the lower side. That is to say, in FIG. 9, the stopcock 5 is in the setting that brings the first flow channel 33 into communication with the first hole 37.

In the state shown in FIG. 9, when the piston 31 (FIG. 2) of the syringe 30 is pushed in the direction of arrow "a", the drug solution in the syringe 30 is expelled into the inner space 16a of the horizontal tubular portion 16. The drug solution that has reached the inner space 16a flows in the direction of arrow "e" and passes through the first flow channel 33 and the first hole 37 to reach the inner spaces 28 of the connecting tubular portion 21 and the upright tubular portion 25. The drug solution that has reached the inner spaces 28 flows to the connecting port 40 as indicated by arrow "g" and is injected into the drug solution bag 10.

In this case, an amount of the drug solution corresponding to the amount by which the piston 31 is pushed is injected into the drug solution bag 10. Therefore, the amount of the drug solution to be injected into the drug solution bag 10 can be adjusted by adjusting the amount by which the piston 31 is pushed while looking at the scale on the cylinder 32. That is to say, a required amount of the drug solution can be injected into the drug solution bag 10 with precision.

A required amount of the drug solution can be injected into the drug solution bag 10 through the process as described above. The drug solution in the drug solution bag 10 will be administered into the body via a tube with a needle with which a port portion 60 (FIG. 1) is pierced.

In the present embodiment, an example in which the syringe 30 (FIG. 2) and the connector main body 2 are separate components has been described. However, a configuration in which the cylinder portion 32 of the syringe 30 and the connector main body 2 are integral with each other also may be employed. For the cylinder portion 32 and the connector main body 2 to be integral with each other, the cylinder portion 32 may be molded integrally with the horizontal tubular portion 16 (FIG. 3), or the cylinder portion 32 may be fixed to the horizontal tubular portion 16 (FIG. 3) with an adhesive. This configuration eliminates the need for attachment of the syringe 30 and facilitates assembly of the connector 1 prior to operation. Moreover, erroneous detachment of the syringe 30 and resulting opening of the other end of the horizontal tubular portion 16 can be prevented.

Moreover, in the present embodiment, as shown in FIG. 3, the lever 8 extended from the stopcock 5 is formed on the stopcock 5. It is possible to determine the status of the flow channel setting within the connector 1 from the orientation of the lever 8.

Specifically, in FIG. 6, the first hole 37 and the first flow channel 33 are in communication with each other. A leading end 8a of the lever 8 points to an external space side communicating with the first hole 37, that is, the connecting port 40 side. Thus, it is possible to determine that the connector 1 is in a state in which it enables transfer to/from the drug solution bag 10 side because the leading end 8a of the lever 8 points to the connecting port 40 side.

In FIG. 7, the second hole 43 and the first flow channel 33 are in communication with each other. The leading end 8a of the lever 8 points to an external space side communicating with the second hole 43, that is, the vial 20 side. Thus, it is possible to determine that the connector 1 is in a state in which it enables transfer to/from the vial 20 side because the leading end 8a of the lever 8 points to the vial 20 side.

That is to say, with the stopcock 5 equipped with the lever 8 according to the present embodiment, it is possible to readily determine which of the drug solution bag 10 side and the vial 20 side the connector 1 enables transfer to/from by observing the orientation of the leading end 8a of the lever 8.

Moreover, the orientation of the leading end 8a of the lever 8 may be reversed from that of the example shown in FIG. 6. In this case, the leading end 8a of the lever 8 in FIG. 6 will point to the vial 20 side, and the leading end 8a of the lever 8 in FIG. 7 will point to the connecting port 40 side of the drug solution bag 10. This means that the leading end 8a of the lever 8 indicates the side on which liquid flow is stopped. Therefore, in this case, it is possible to readily determine which of the drug solution bag 10 side and the vial 20 side the connector 1 stops liquid transfer to/from by observing the orientation of the leading end 8a of the lever 8.

Next, a structure for connecting the first connecting portion 3 to the drug solution bag 10 will be described with reference to FIGS. 10 and 11. FIG. 10 is a cross-sectional view showing a state before the first connecting portion 3 is connected to the drug solution bag 10. As described above, the connecting port 40 is attached to the drug solution bag 10. The port portion 41 is attached to the leading end portion of the connecting port 40. The septum (the partition) 42 in which a slit 45 is formed is attached to the port portion 41.

The first connecting portion 3 shown in FIG. 10 corresponds to a cross-sectional view taken along line BB in FIG. 3. The lever locks 12 are integral with the first connecting portion 3. Bending the lower portions of the lever locks 12 toward a central axis 11a of the connecting port 11 (the direction of arrow "c") causes the claw portions 13 of the lever locks 12 to be displaced away from the central axis 11a of the connecting port 11 (the direction of arrow "h").

FIG. 11 is a cross-sectional view showing a state in which the first connecting portion 3 has been connected to the port portion 41. The port portion 41 is inserted in the connecting port 11, and also the claw portions 13 of the lever locks 12 are engaged with the end face 41a of the port portion 41. During insertion of the port portion 41 into the connecting port 11, in FIG. 10, the lower portions of the lever locks 12 are bent toward the central axis 11a of the connecting port 11 (the direction of arrow "c"), and thus, the claw portions 13 of the lever locks 12 are displaced away from the central axis 11a of the connecting port 11 (the direction of arrow "h"). Accordingly, once the port portion 41 is inserted into the connecting port 11, the claw portions 13 engage the end face 41a of the port portion 41 as shown in FIG. 11.

Here, in FIG. 10, the upright tubular portion 25 that is integral with the first connecting portion 3 is covered with a shield 26 that can open and close by extension and retraction. A slit 27 is formed in the shield 26. When the shield 26 is retracted, a portion where the slit 27 is formed opens (FIG. 11), and when the retracted shield 26 is restored, the portion where the slit 27 is formed closes (FIG. 10).

In the state shown in FIG. 10, the shield 26 covers the upright tubular portion 25, whereas in the state shown in FIG. 11, the shield 26 is retracted, and the upright tubular portion 25 extends outside the shield 26. This is because during insertion of the port portion 41 into the connecting port 11, a lower portion of the port portion 41 presses against the shield 26 such that the shield is pushed down.

A leading end portion of the upright tubular portion 25 extending outside the shield 26 pushes up the septum 42 attached to the port portion 41 and thus forces the slit 45 (FIG. 10) of the septum 42 open. As a result, the inner space of the connecting port 40 is brought into communication with the inner spaces 28 of the upright tubular portion 25 and the connecting tubular portion 21.

Next, after a required amount of the drug solution has been injected into the drug solution bag 10, the first connecting portion 3 that is integral with the vial 20 is to be detached from the port portion 41. During detachment, in FIG. 11, the lower portions of the lever locks 12 can be pressed against toward the central axis 11a of the connecting port 11 (the direction of arrow "c"), and the claw portions 13 of the lever locks 12 displaced away from the central axis 11a of the connecting port 11 (the direction of arrow "h").

The first connecting portion 3 returns to the state shown in FIG. 10 after being detached from the port portion 41. In the state shown in FIG. 10, the retracted shield 26 has been restored and covers the upright tubular portion 25 again. In this state, leakage of the drug solution in the vial 20 is prevented.

It should be noted that, in FIG. 10, the structure of the upright tubular portion 25 covered with the shield 26 may be provided on the port portion 41 side. In this case, the structure in which the opening is covered with the septum 42 that can open and close by extension and retraction will be provided in the first connecting portion 3. According to this configuration, in FIG. 11, although the vertical relationship between the upright tubular portion 25 and the septum 42 is inverted, the fact remains that the inner space of the connecting port 40 is brought into communication with the inner space 28 of the connecting tubular portion 21.

Moreover, the first connecting portion 3 of the present embodiment is merely an example, and various types of connecting systems can be employed. Furthermore, although an example in which the first connecting portion 3 and the connector main body 2 are configured as separate components has been described, a configuration in which the first connecting portion 3 and the connector main body 2 are integrally molded is conceivable depending on the structure of the first connecting portion 3.

Figure 12:
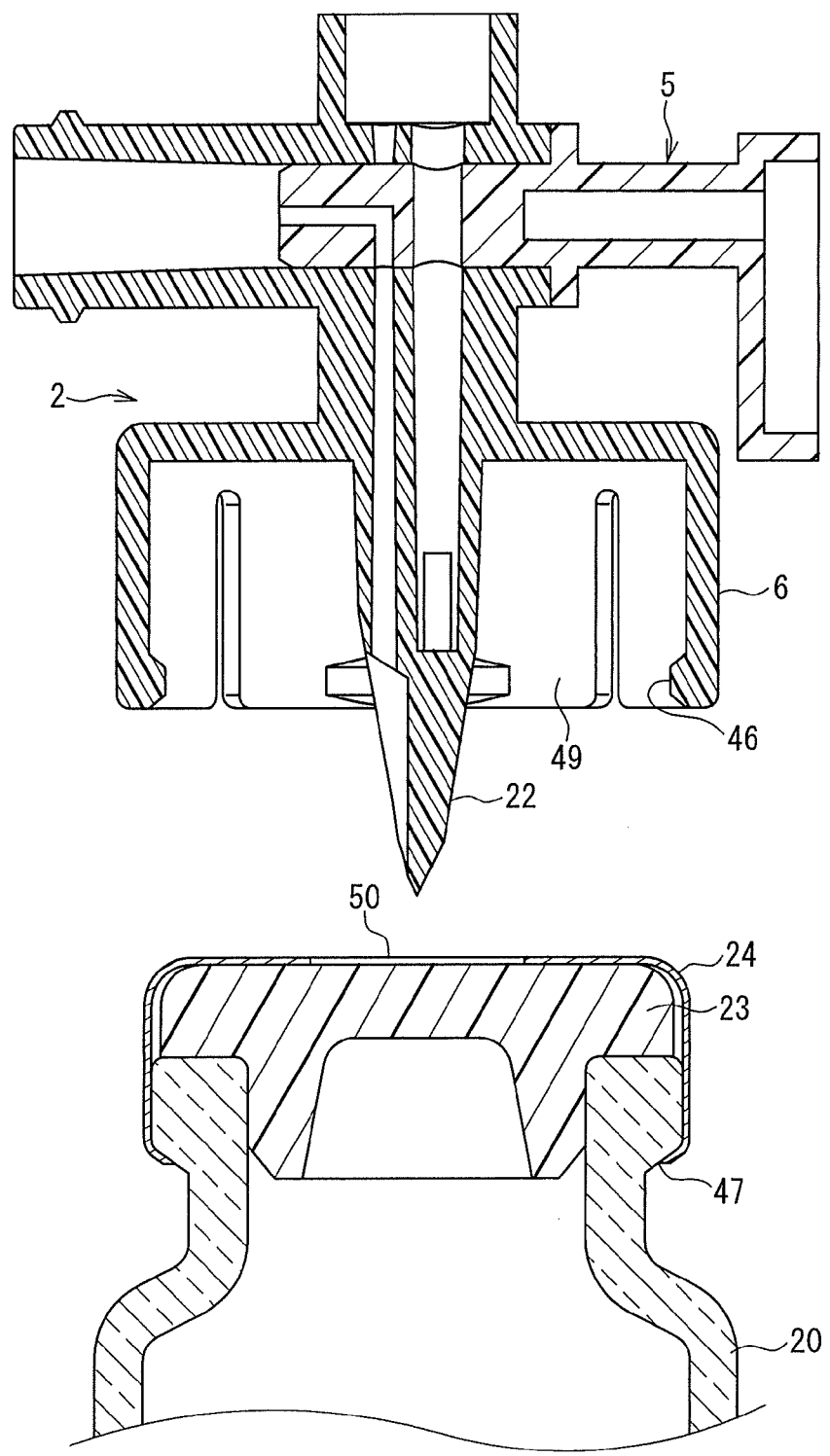
FIG. 12 is a cross-sectional view showing a state before a second connecting portion 6 according to the embodiment of the present invention is connected to the vial 20.

Next, a structure for connecting the second connecting portion 6 to the vial 20 will be described with reference to FIGS. 12 and 13. FIG. 12 is a cross-sectional view showing a state before the second connecting portion 6 is connected to the vial 20. The opening of the vial 20 is sealed with the cap 24 via the rubber stopper 23.

An opening 50 is formed in a central portion of the cap 24. Thus, the rubber stopper 23 is exposed at the position of the opening 50.

A protrusion 46 protruding from an inner circumferential surface of the connecting port 49 is formed in the connecting port 49 of the second connecting portion 6. An expanded-diameter portion 47 is formed on the opening side of the vial 20. As will be described later by means of FIG. 13, the protrusion 46 of the second connecting portion 6 is to be engaged with the expanded-diameter portion 47 of the vial 20.

Figure 13:
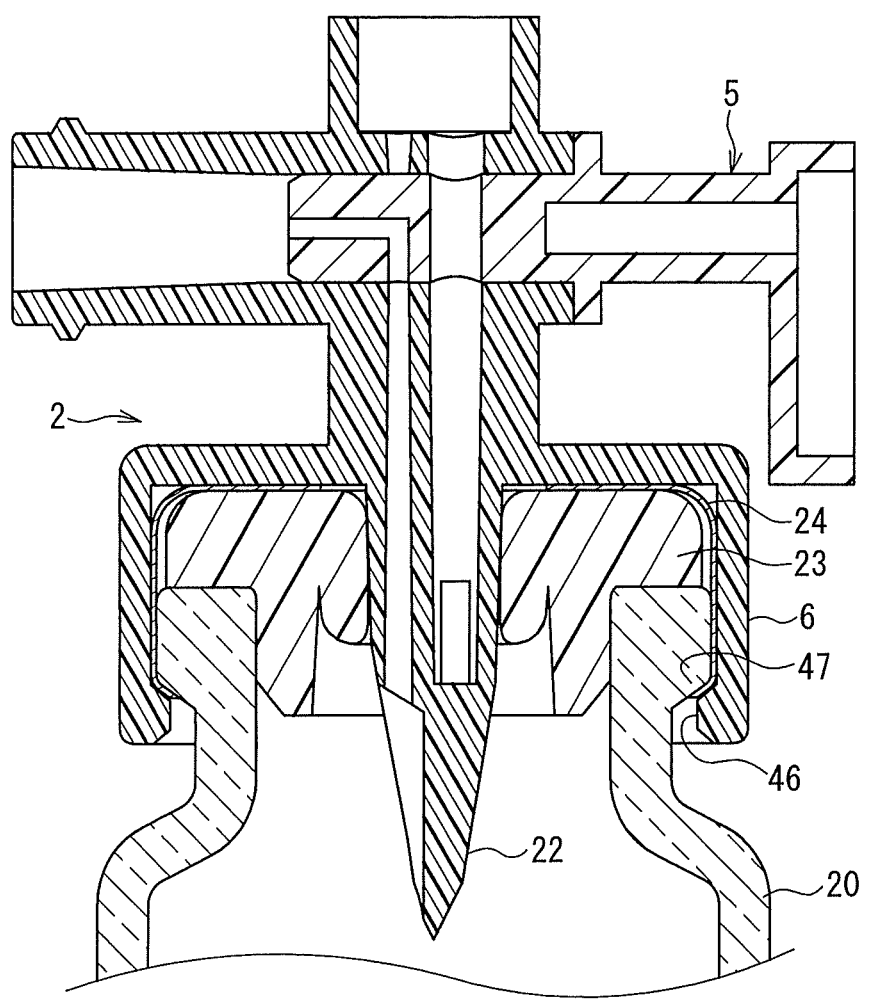
FIG. 13 is a cross-sectional view showing a state in which the second connecting portion 6 according to the embodiment of the present invention has been connected to the vial 20.

FIG. 13 is a cross-sectional view showing a state in which the second connecting portion 6 has been connected to the vial 20. An inner circumferential surface of the second connecting portion 6 and an outer circumferential surface of the cap 24 of the vial 20 are fitted to each other. As shown in FIGS. 3 and 4, slits 48 are formed in a side wall portion of the second connecting portion 6 and facilitate fitting of the second connecting portion 6 to the vial 20.

In FIG. 13, the rubber stopper 23 of the vial 20 is pierced with the needle-like portion 22 that is integral with the connector main body 2. The protrusion 46 of the second connecting portion 6 is engaged with the expanded-diameter portion 47 of the vial 20, and this prevents the second connecting portion 6 from falling off the vial 20.

Moreover, unlike the first connecting portion 3, the second connecting portion 6 is not provided with a mechanism that facilitates disconnection, such as the lever locks 12. For this reason, once the second connecting portion 6 is firmly fitted to the vial 20, the second connecting portion 6 can be prevented from readily falling off the vial 20. Thus, leakage of the drug solution due to easy detachment of the vial 20 can be prevented.

Moreover, after the first connecting portion 3 has been detached from the drug solution bag 10, as shown in FIG. 10, the upright tubular portion 25 is covered with the shield 26. Therefore, leakage of the drug solution from the upright tubular portion 25 is prevented even after detachment of the first connecting portion 3 from the drug solution bag.

Thus, if the vial 20 is disposed of in a state in which the first connecting portion 3 has been detached from the drug solution bag 10 and the second connecting portion 6 and the vial 20 remain in the connected state, leakage of the drug in the vial 20 is prevented.

The drug leakage preventing structure as described above is particularly effective in the case where the drug in the vial 20 is a highly toxic drug such as an anticancer agent.

It should be noted that the second connecting portion 6 of the present embodiment is merely an example, and various types of connecting systems can be employed. Moreover, although the second connecting portion 6 is formed integrally with the connector main body 2, the second connecting portion 6 may be configured as a component separate from the connector main body 2 as long as a structure that prevents the second connecting portion 6 from readily falling off the connector main body 2 can be achieved.

Embodiment 2

Hereinafter, a connector according to Embodiment 2 of the present invention will be described with reference to the drawings. The portions having the same configuration as those of Embodiment 1 are denoted by the same reference numerals, and detailed descriptions thereof are omitted.

Figure 14:
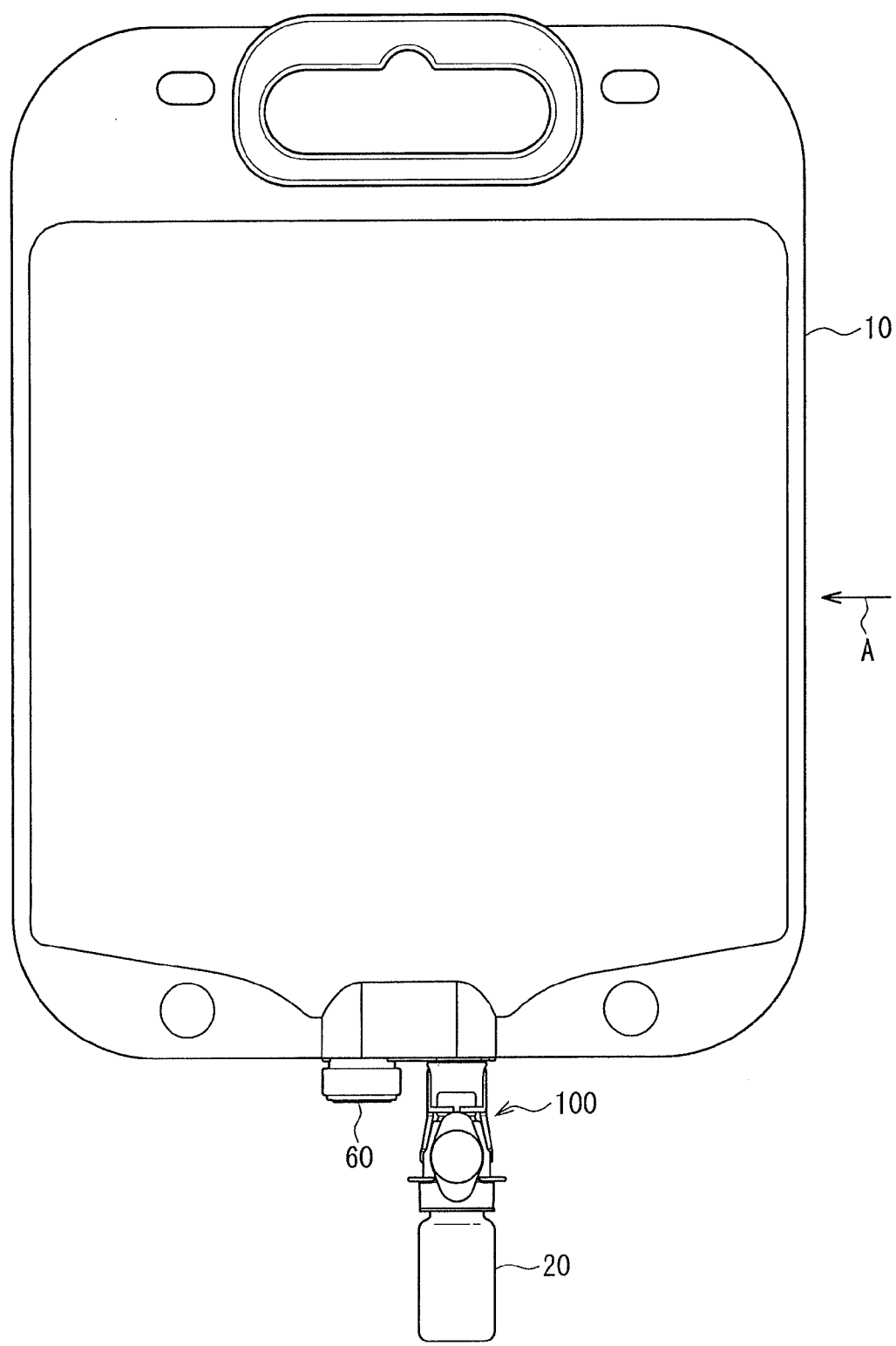
FIG. 14 is a diagram showing an example of use of a connector 100 according to Embodiment 2 of the present invention.

FIG. 14 is a diagram showing an example of use of a connector 100 according to Embodiment 2 of the present invention. In the example shown in this diagram, the drug solution bag 10 and the vial 20 are connected to each other via the connector 100.

Figure 15:
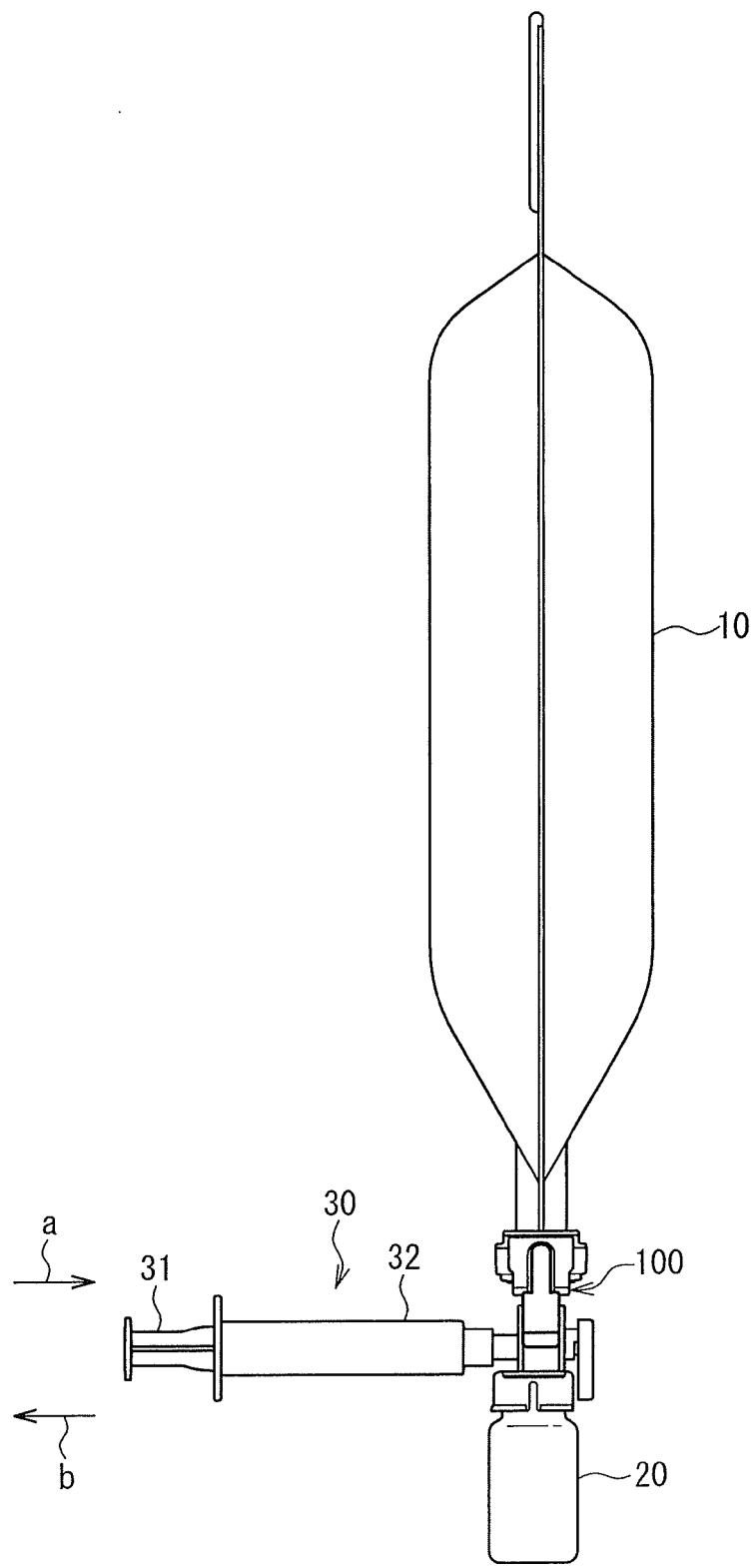
FIG. 15 is a diagram showing the example in FIG. 14 as seen from the direction of arrow A.

FIG. 15 shows the example in FIG. 14 as seen from the direction of arrow A. The syringe 30 is attached to the connector 100. As is the case with Embodiment 1, pushing the piston 31 in the direction of arrow "a" can cause a liquid in the cylinder 32 to be ejected from the leading end of the cylinder 32. On the other hand, pulling the piston 31 in the direction of arrow "b" can cause a liquid to be drawn into the cylinder 32.

Figure 16:
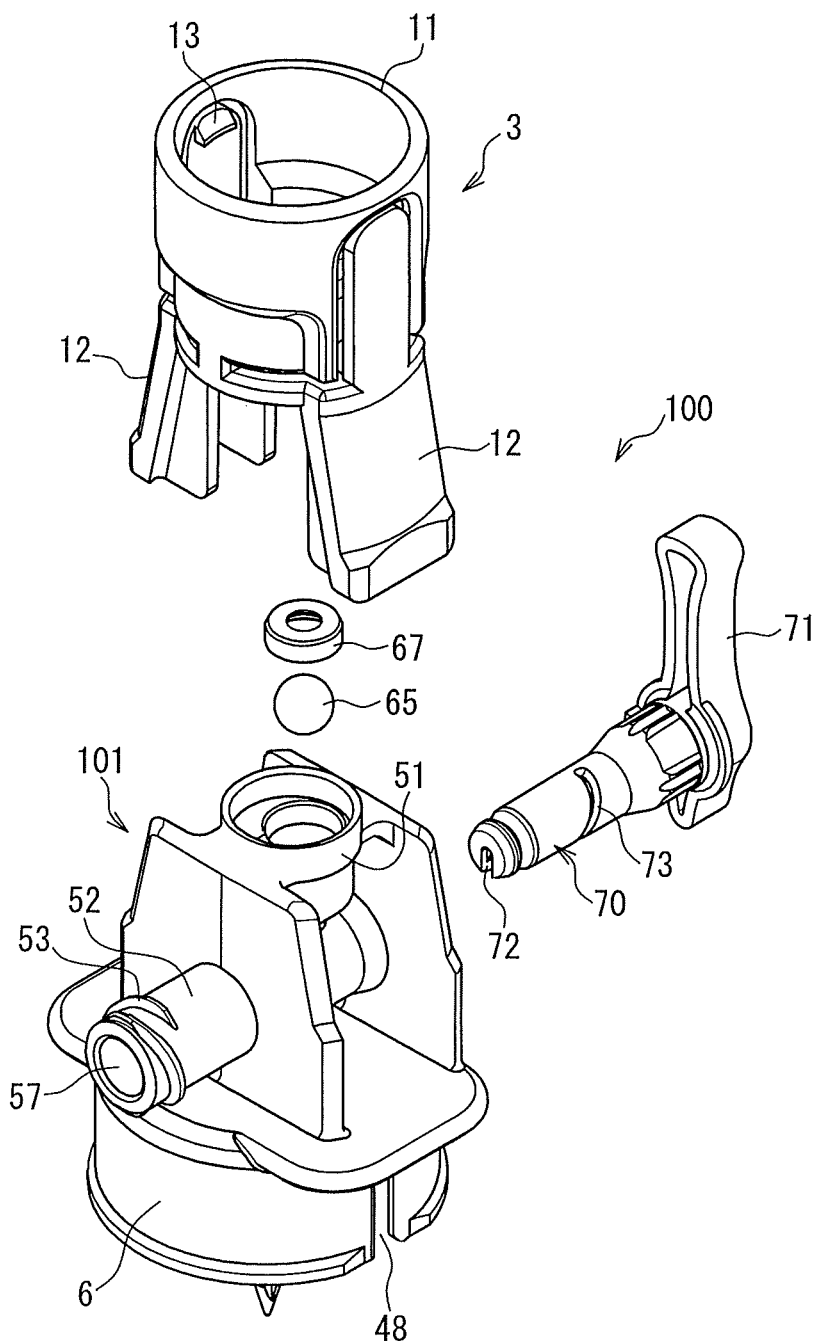
FIG. 16 is an exploded perspective view of the connector 100 according to Embodiment 2 of the present invention.

FIG. 16 is an exploded perspective view of the connector 100. As shown in FIG. 16, the connector 100 can be disassembled into a connector main body 101, the first connecting portion 3, and a stopcock 70. The connector main body 101 is integral with the second connecting portion 6.

It should be noted that in the following description, the portion denoted by reference numeral 101 in FIG. 16 is referred to as the connector main body 101. However, this is for the sake of convenience, and the connector main body 101 and the first connecting portion 3 connected thereto may be regarded collectively as the connector main body 101.

The first connecting portion 3 is a connector for connecting the connector 100 to the drug solution bag 10 (FIG. 14). The first connecting portion 3 has the same basic configuration as the first connecting portion 3 of Embodiment 1, even though they are partly different in shape. Connection of the first connecting portion 3 to the drug solution bag 10 is the same as described in Embodiment 1 by means of FIGS. 10 and 11.

The connector main body 101 includes an axial tubular portion 51 and a horizontal tubular portion 52 intersecting with each other. A thread 53 is formed on the horizontal tubular portion 52 for the purpose of screwing to the syringe 30 (FIG. 15). The cylindrical stopcock 70 is inserted into the horizontal tubular portion 52. When a lever 71 is rotated, the stopcock 70 rotates around an axis of the horizontal tubular portion 52.

The connector 100, in a connected state as shown in FIG. 15, transfers a liquid between the drug solution bag 10 and the vial 20 via the syringe 30. By rotating the stopcock 70 (FIG. 16), it is possible to switch between the setting that allows liquid transfer between the drug solution bag 10 and the syringe 30 and the setting that allows liquid transfer between the vial 20 and the syringe 30. Details of this switching will be described later with reference to FIGS. 19 to 22.

As described above, in FIG. 16, the connector main body 101 is integral with the second connecting portion 6. The second connecting portion 6 is for connecting the connector main body 101 to the vial 20. The second connecting portion 6 has the same basic configuration as the second connecting portion 6 of Embodiment 1, even though they are partly different in shape. During connection of the second connecting portion 6 to the vial 20, the cap portion of the vial 20 is fitted into the connecting port 49 (FIG. 17) of the second connecting portion 6. Details of this connection are the same as described in Embodiment 1 by means of FIGS. 12 and 13.

Figure 17:
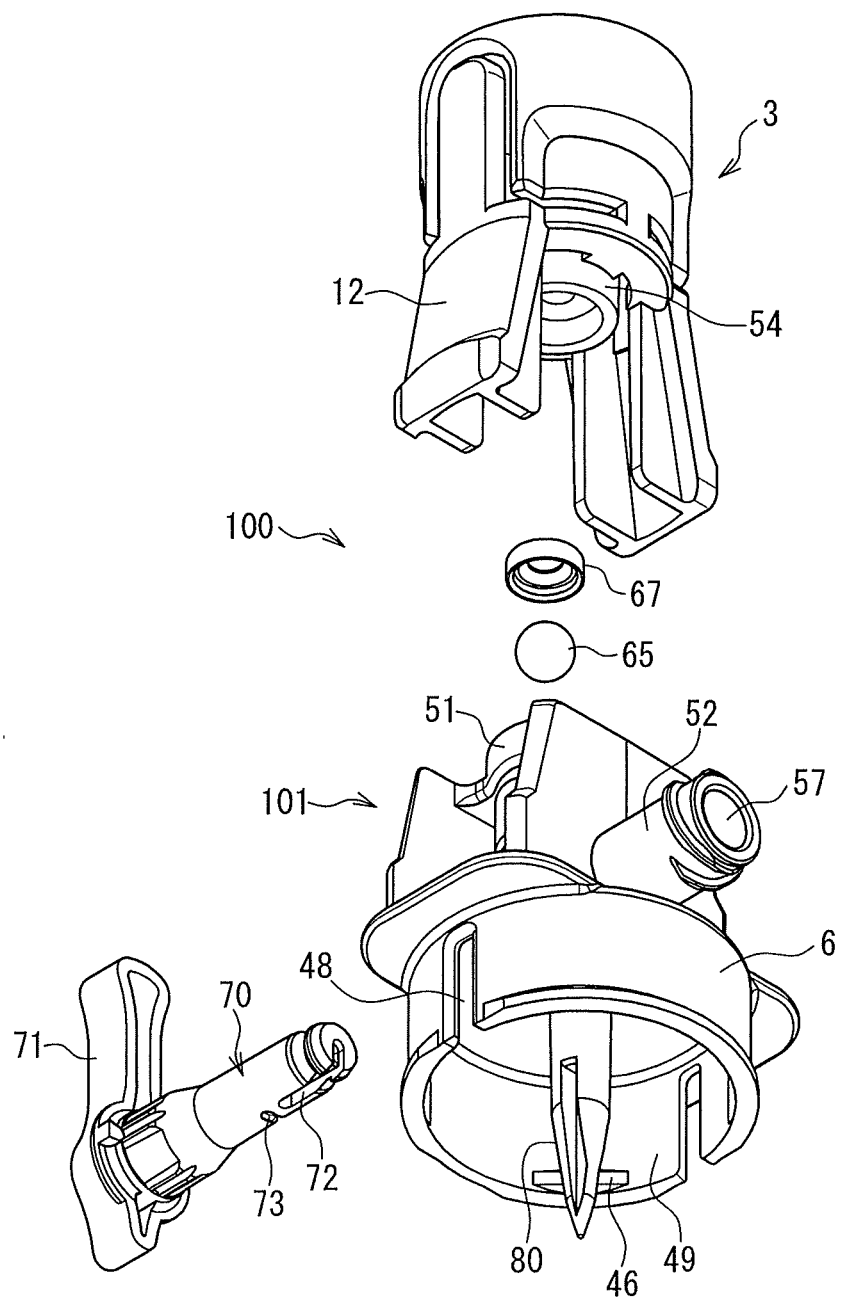
FIG. 17 is an exploded perspective view of the connector 100 in FIG. 16 as seen from a different angle from that of FIG. 16.

FIG. 17 is an exploded perspective view of the connector 100 as seen from a different angle from that of FIG. 16. FIG. 17 shows a back side of the first connecting portion 3 and the connector main body 101. A connecting tubular portion 54 is formed on the back side of the first connecting portion 3. The first connecting portion 3 can be connected to the connector main body 101 by fitting an outer circumferential surface of this connecting tubular portion 54 to an inner circumferential surface (FIG. 16) of the axial tubular portion 51 of the connector main body 101.

A needle-like portion 80 is formed on the back side of the connector main body 101. The needle-like portion 80 has a sharp tip, and the rubber stopper 23 (FIG. 18) of the vial 20 can be pierced with the needle-like portion 80.

As shown in FIGS. 16 and 17, a first flow channel 72 and a second flow channel 73 are formed in the stopcock 70. The first flow channel 72 and the second flow channel 73 are also shown in cross-sectional views in FIGS. 19 to 22. The first flow channel 72 is a recess formed in a side face of the stopcock 70, and this recess extends to a leading end face of the stopcock 70. Thus, a notch is formed in the leading end face of the stopcock 70.

Figure 19:
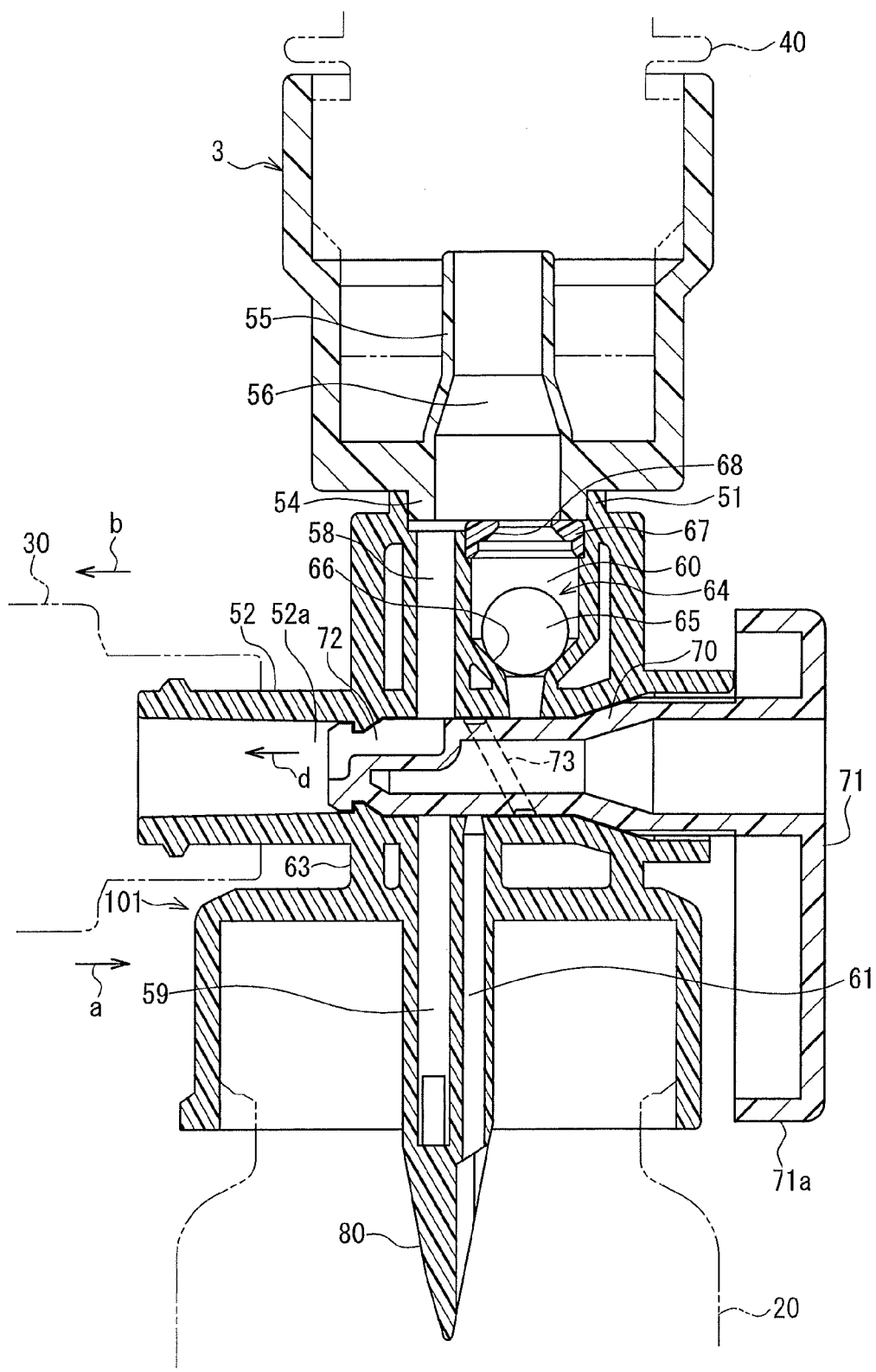
FIG. 19 is a cross-sectional view showing a state in which a solvent in the drug solution bag is drawn into the syringe 30 from the connecting port 40, according to Embodiment 2 of the present invention.

The ends of the second flow channel 73 are located at mutually different positions both in an axial direction and in a circumferential direction of the stopcock 70, as shown in FIGS. 16, 17, and 19. In the present embodiment, a recess formed into a spiral shape is described as an example.

Figure 18:
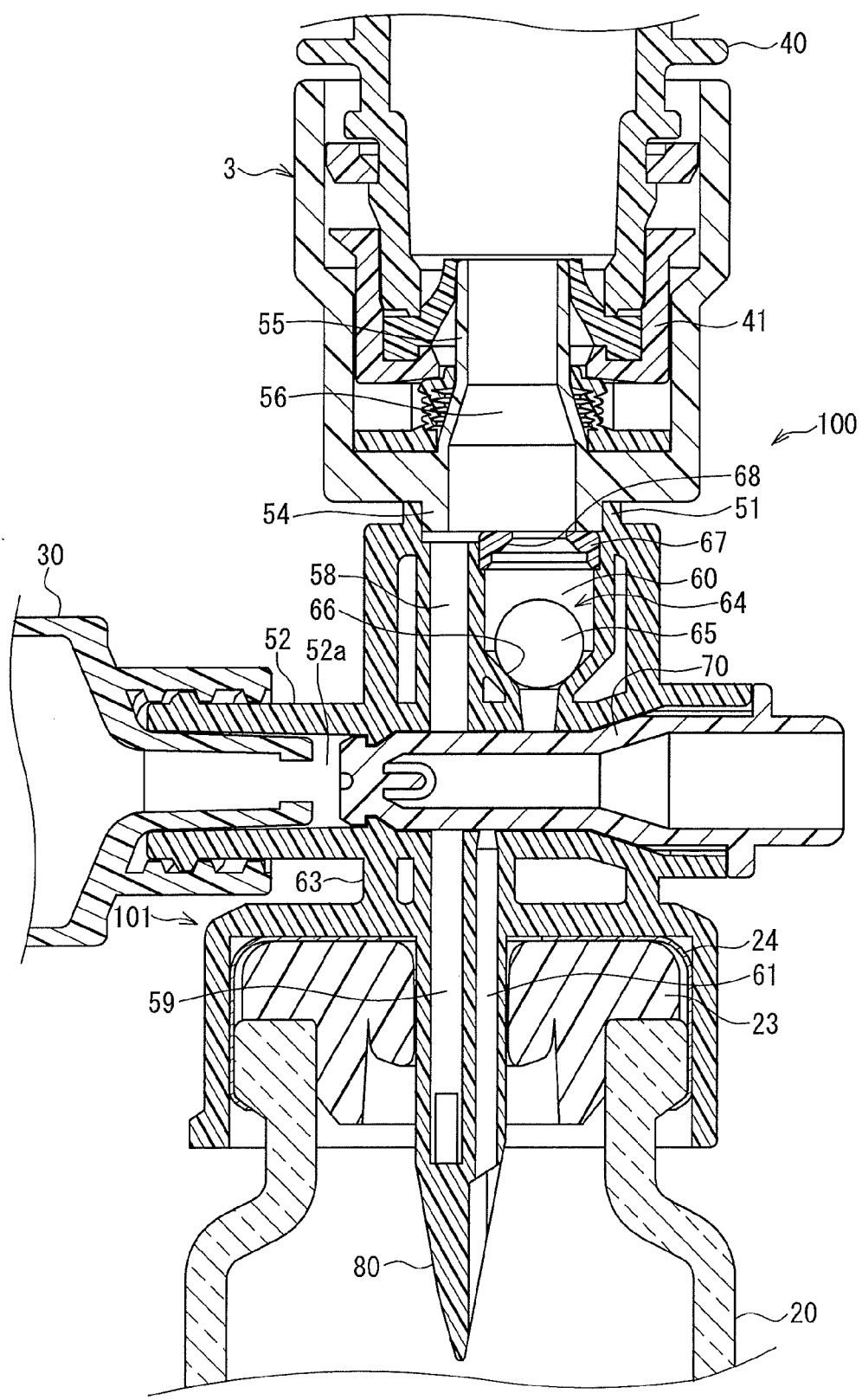
FIG. 18 is a cross-sectional view of the connector 100 according to Embodiment 2 of the present invention.

FIG. 18 shows a cross-sectional view of the connector 100. This cross-sectional view corresponds to a vertical cross-sectional view of the connector 100 and its peripheral portions shown in FIG. 15. The first connecting portion 3 is connected to the port portion 41 that is attached to the leading end portion of the connecting port 40 attached to the drug solution bag 10. Details of this connection are the same as described in Embodiment 1 with reference to FIGS. 10 and 11.

The outer circumferential surface of the connecting tubular portion 54 of the first connecting portion 3 is fitted to the inner circumferential surface of the axial tubular portion 51 of the connector main body 101. Thus, the first connecting portion 3 is connected to the connector main body 101.

The stopcock 70 is inserted in the horizontal tubular portion 52 of the connector main body 101. One end of the horizontal tubular portion 52 is sealed with the stopcock 70, and an open portion 57 (FIGS. 16 and 17) is formed at the other end of the horizontal tubular portion 52.

A first hole 58 and a second hole 59 are formed in the connector main body 101. These two holes are both holes that bring an inner space 52a of the horizontal tubular portion 52 into communication with an external space of the connector main body 101. The first hole 58 passes through a side wall portion of the horizontal tubular portion 52, and the second hole 59 passes through a base portion 63 and the needle-like portion 80.

Furthermore, a third hole 60 and a fourth hole 61 are formed in the connector main body 101. These two holes are also holes that bring the inner space 52a of the horizontal tubular portion 52 into communication with the external space of the connector main body 101 as is the case with the first hole 58 and the second hole 59. The third hole 60 passes through the side wall portion of the horizontal tubular portion 52, and the fourth hole 61 passes through the base portion 63 and the needle-like portion 80.

A check valve 64 is provided in the third hole 60. The check valve 64 includes a ball 65, an inclined surface 66, and an inclined surface 68 that is formed in a cap 67. In the state shown in FIG. 18, the ball 65 is in contact with the inclined surface 66 under its own weight. Thus, even in a setting that brings the third hole 60 into communication with the fourth hole 61 via the second flow channel 73 as shown in FIG. 20, liquid transfer through the third hole 60 and the fourth hole 61 is stopped, so that the flow of the solvent moving from the drug solution bag 10 side toward the vial 20 side is stopped.

Figure 20:
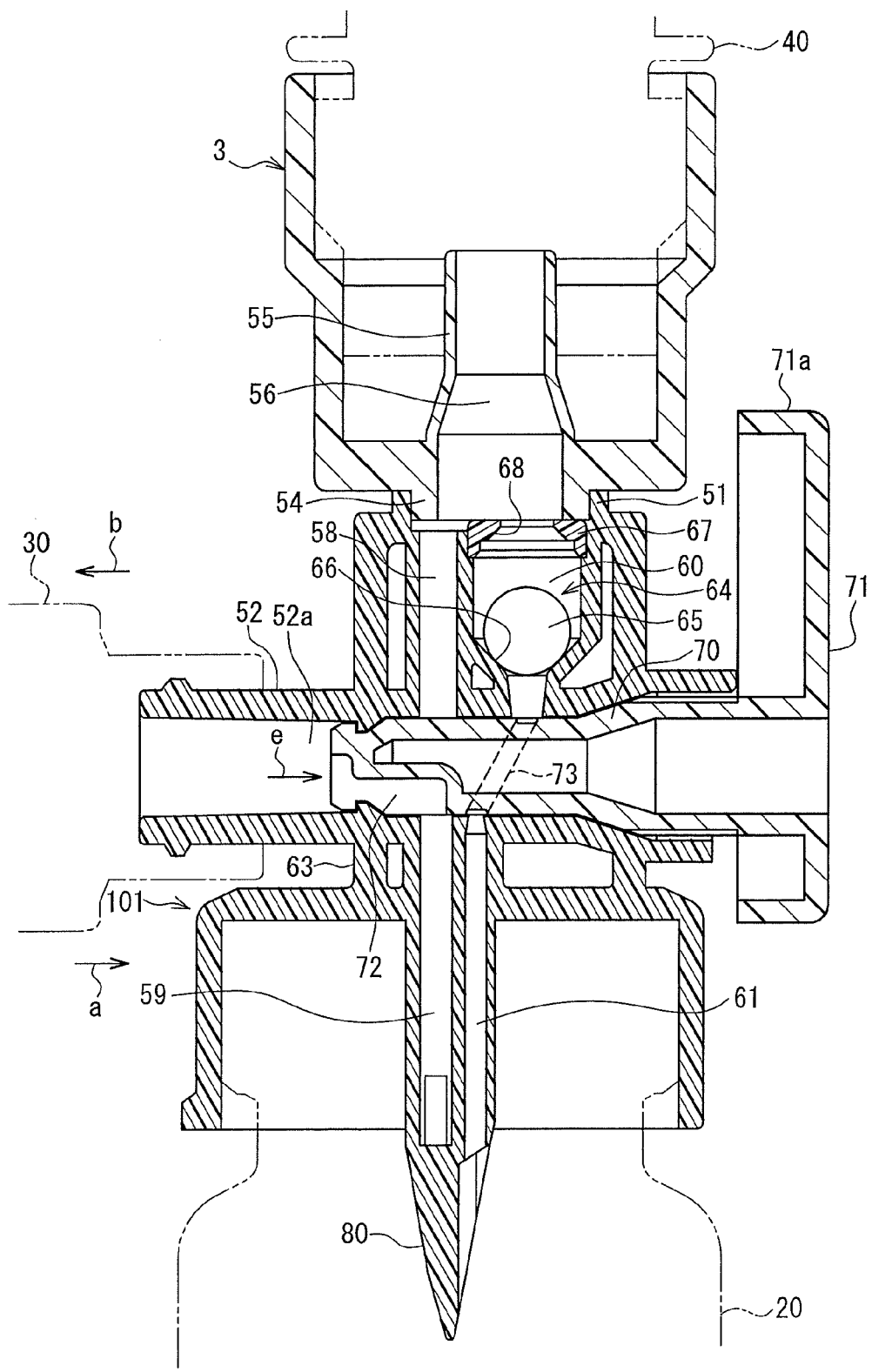
FIG. 20 is a cross-sectional view showing a state in which the solvent that has been drawn into the syringe 30 is injected into the vial 20, according to Embodiment 2 of the present invention.
Figure 21:
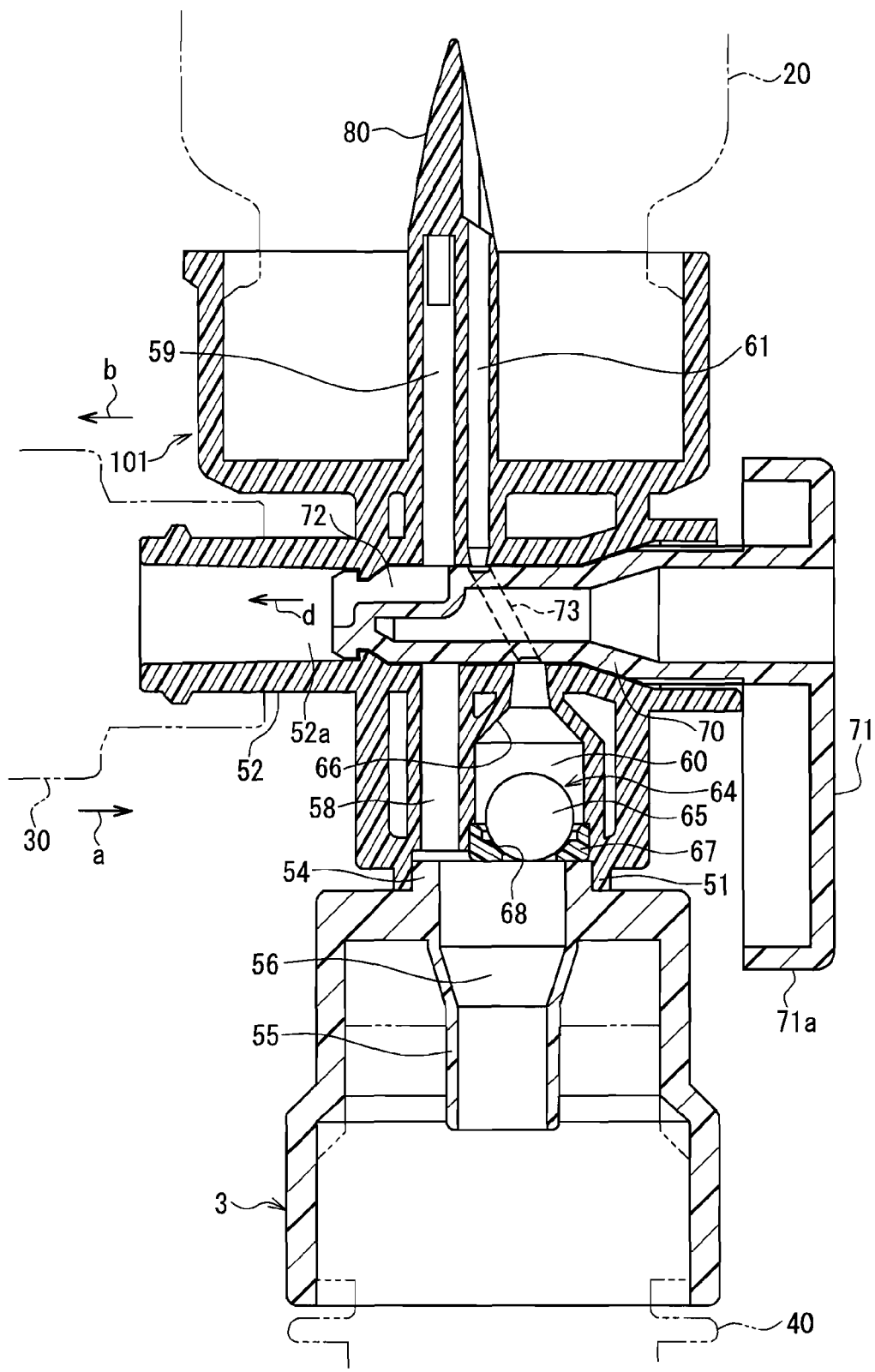
FIG. 21 is a cross-sectional view showing a state in which a drug solution that has been generated within the vial 20 is drawn into the syringe 30, according to Embodiment 2 of the present invention.

On the other hand, when the connector is inverted from the state shown in FIG. 20, the ball 65 comes into contact with the inclined surface 68 of the cap 67 under its own weight, as shown in FIG. 21. In this case, liquid transfer through the third hole 60 is stopped, so that the flow of the drug solution moving from the vial 20 side toward the drug solution bag 10 side is stopped.

Therefore, with the check valve 64, liquid transfer through both of the third hole 60 and the fourth hole 61 is stopped even in the setting that brings the third hole 60 into communication with the fourth hole 61 via the second flow channel 73. Thus, in the case where the syringe 30 is erroneously operated, the liquid is prevented from directly going into the drug solution bag 10 or the vial 20 without passing through the syringe 30. Details of this will be described later with reference to FIGS. 20 and 21.

Although not illustrated in FIG. 18, the lever 71 (FIGS. 16 and 17) is formed on the stopcock 70. When the lever 71 is rotated, it rotates around the axis of the horizontal tubular portion 52. Integrally with this rotation, the first flow channel 72 and the second flow channel 73 (FIGS. 16 and 17) formed in the stopcock 70 also rotate.

In the state shown in FIG. 18, leading end portions of the first to the fourth holes 58 to 61 on the horizontal tubular portion 52 side are obstructed by the side face of the stopcock 70. Thus, liquid transfer between the inner space 52a of the horizontal tubular portion 52 and the external space of the connector main body 101 via the first to the fourth holes 58 to 61 is blocked.

By rotating the lever 71 (FIGS. 16 and 17), it is possible to switch between a setting that brings the inner space 52a of the horizontal tubular portion 52 into communication with the first hole 58 via the first flow channel 72 (FIGS. 16 and 17) in the stopcock 70 and a setting that brings the inner space 52a of the horizontal tubular portion 52 into communication with the second hole 59 via the first flow channel 72 and also brings the third hole 60 into communication with the fourth hole 61 via the second flow channel 73 (FIGS. 16 and 17). This switching between the settings can be used to transfer a solvent in the drug solution bag 10 into the vial 20 to generate a drug solution by dissolving a drug in powder form contained in the vial 20 in the solvent, and afterward to inject this drug solution into the drug solution bag 10.

Hereinafter, an operating procedure during injection of the drug in the vial 20 into the drug solution bag 10 will be described with reference to FIGS. 19 to 22. In the drawings described below, the connecting port 40, the port portion 41, the syringe 30, and the vial 20 in FIG. 18 are shown simplified in chain double-dashed lines for clarity of illustration.

FIG. 19 is a cross-sectional view showing a state in which the solvent in the drug solution bag 10 is drawn into the syringe 30 from the connecting port 40. In FIG. 19, the stopcock 70 is in the setting that brings the first hole 58 into communication with the inner space 52a of the horizontal tubular portion 52 via the first flow channel 72 in the stopcock 70. Accordingly, the solvent in the drug solution bag 10 can flow to the inner space 52a of the horizontal tubular portion 52 through the connecting port 40, an inner space 56 of an upright tubular portion 55, the first hole 58, and the first flow channel 72.

When the stopcock 70 is in the setting shown in FIG. 19, pulling the piston 31 (FIG. 15) of the syringe 30 in the direction of arrow "b" can cause the solvent in the drug solution bag 10 to be drawn into the inner space 52a of the horizontal tubular portion 52 and further into the syringe 30 (the direction of arrow "d").

In this case, an amount of the solvent corresponding to the amount by which the piston 31 is pulled is drawn into the syringe 30. Therefore, the amount of the solvent to be drawn into the syringe 30 can be adjusted by adjusting the amount by which the piston 31 is pulled while looking at the scale on the cylinder 32. That is to say, a required amount of the solvent can be drawn into the syringe 30 with precision.

On the other hand, in the state shown in FIG. 19, the leading end portions of the second hole 59, the third hole 60, and the fourth hole 61 on the horizontal tubular portion 52 side are obstructed by the side face of the stopcock 70. Thus, the solvent in the drug solution bag 10 is prevented from directly flowing into the vial 20.

FIG. 20 is a cross-sectional view showing a state in which the solvent that has been drawn into the syringe 30 is injected into the vial 20. The setting of the stopcock 70 shown in FIG. 20 is different from that in FIG. 19. In FIG. 20, the stopcock 70 has been rotated by rotating the lever 71 from the state shown in FIG. 19. Due to the rotation of the stopcock 70, the first flow channel 72 that is integral with the stopcock 70 also moves rotationally. In FIG. 19, the first flow channel 72 is positioned on the upper side, whereas in FIG. 20, the first flow channel 72 is positioned on the lower side. That is to say, in FIG. 20, the stopcock 70 is in the setting that brings the inner space 52a of the horizontal tubular portion 52 into communication with the second hole 59 via the first flow channel 72.

Moreover, due to the rotation of the stopcock 70, the second flow channel 73 that is integral with the stopcock 70 also moves rotationally. In FIG. 19, both of the ends of the second flow channel 73 are obstructed by an inner circumferential surface of the horizontal tubular portion 52, whereas in FIG. 20, the ends of the second flow channel 73 communicate with the third hole 60 and the fourth hole 61, respectively.

In the state shown in FIG. 20, when the piston 31 (FIG. 15) of the syringe 30 is pushed in the direction of arrow "a", the solvent in the syringe 30 is expelled into the inner space 52a of the horizontal tubular portion 52. The solvent that has reached the inner space 52a flows in the direction of arrow "e" and passes through the first flow channel 72 and the second hole 59 to be injected into the vial 20.

In this case, an amount of the solvent corresponding to the amount by which the piston 31 is pushed flows out of the syringe 30. Thus, the amount of the solvent to be caused to flow out of the syringe 30 can be adjusted by adjusting the amount by which the piston 31 is pushed while looking at the scale on the cylinder 32. That is to say, a required amount of the solvent can be injected into the vial 20 with precision.

During injection of the solvent into the vial 20, air in the vial 20 passes up through the fourth hole 61 and flows into the drug solution bag 10 via the second flow channel 73, the third hole 60, and the inner space 56 of the upright tubular portion 55. The air that has flowed into the third hole 60 pushes up the ball 65, so that the air can flow from the third hole 60 toward the upright tubular portion 55 side.

Here, in the state shown in FIG. 20, if the piston 31 (FIG. 15) of the syringe 30 is pulled in the direction of arrow "b" instead of being pushed in the direction of arrow "a", air in the vial 20 will be drawn into the syringe 30 via the second hole 59. This causes the solvent in the drug solution bag 10 to flow so as to be drawn into the vial 20 side, that is, drawn into the third hole 60 side.

On the other hand, in the state shown in FIG. 20, the ball 65 is in contact with the inclined surface 66, and downward movement of the ball 65 is restricted. Thus, even when the solvent flows into the third hole 60, the flow of the solvent is stopped in the third hole 60, so that the solvent is prevented from passing through the second flow channel 73 and flowing into the vial 20.

That is to say, the check valve 64 that is provided in the third hole 60 prevents the solvent from directly flowing into the vial 20 without passing through the syringe 30 even in the case where the syringe 30 is operated erroneously.

FIG. 21 is a cross-sectional view showing a state in which the drug solution that has been generated within the vial 20 by dissolving the drug in powder form is drawn into the syringe 30. In FIG. 21, the vertical relationship between the connecting port 40 of the drug solution bag 10 and the vial 20 is inverted with respect to that shown in FIGS. 19 and 20. That is to say, in FIGS. 19 and 20, the vial 20 is positioned on the lower side, whereas in FIG. 21, the vial 20 is positioned on the upper side. In this arrangement, the drug solution in the vial 20 can flow to the inner space 52a of the horizontal tubular portion 52 through the second hole 59 and the first flow channel 72.

When the stopcock 70 is in the setting shown in FIG. 21, pulling the piston 31 (FIG. 15) of the syringe 30 in the direction of arrow "b" can cause the drug solution in the vial 20 to be drawn into the inner space 52a of the horizontal tubular portion 52 and further into the syringe 30 (the direction of arrow "d").

In this case, an amount of the drug solution corresponding to the amount by which the piston 31 is pulled is drawn into the syringe 30. Therefore, the amount of the drug solution to be drawn into the syringe 30 can be adjusted by adjusting the amount by which the piston 31 is pulled while looking at the scale on the cylinder 32. That is to say, a required amount of the drug solution can be drawn into the syringe 30 with precision.

During drawing of the drug solution contained in the vial 20 into the syringe 30, air in the drug solution bag 10 passes up through the third hole 60 and flows into the vial 20 via the second flow channel 73 and the fourth hole 61. The air that has flowed into the third hole 60 pushes up the ball 65, so that the air can flow from the third hole 60 toward the second flow channel 73 side.

Here, in the state shown in FIG. 21, if the piston 31 (FIG. 15) of the syringe 30 is pushed in the direction of arrow "a" instead of being pulled in the direction of arrow "b", air or the drug solution will flow backward into the vial 20 via the second hole 59. This causes the drug solution in the vial 20 to flow so as to be expelled to the third hole 60 side via the fourth hole 61 and the second flow channel 73.

On the other hand, in the state shown in FIG. 21, the ball 65 is in contact with the inclined surface 68, and downward movement of the ball 65 is restricted. Thus, even when the drug solution flows into the third hole 60, the flow of the drug solution is stopped in the third hole 60, so that the drug solution is prevented from flowing into the drug solution bag 10 through the second flow channel 73.

That is to say, the check valve 64 that is provided in the third hole 60 prevents the drug solution from directly flowing into the drug solution bag 10 without passing through the syringe 30 even in the case where the syringe 30 is erroneously operated.

Figure 22:
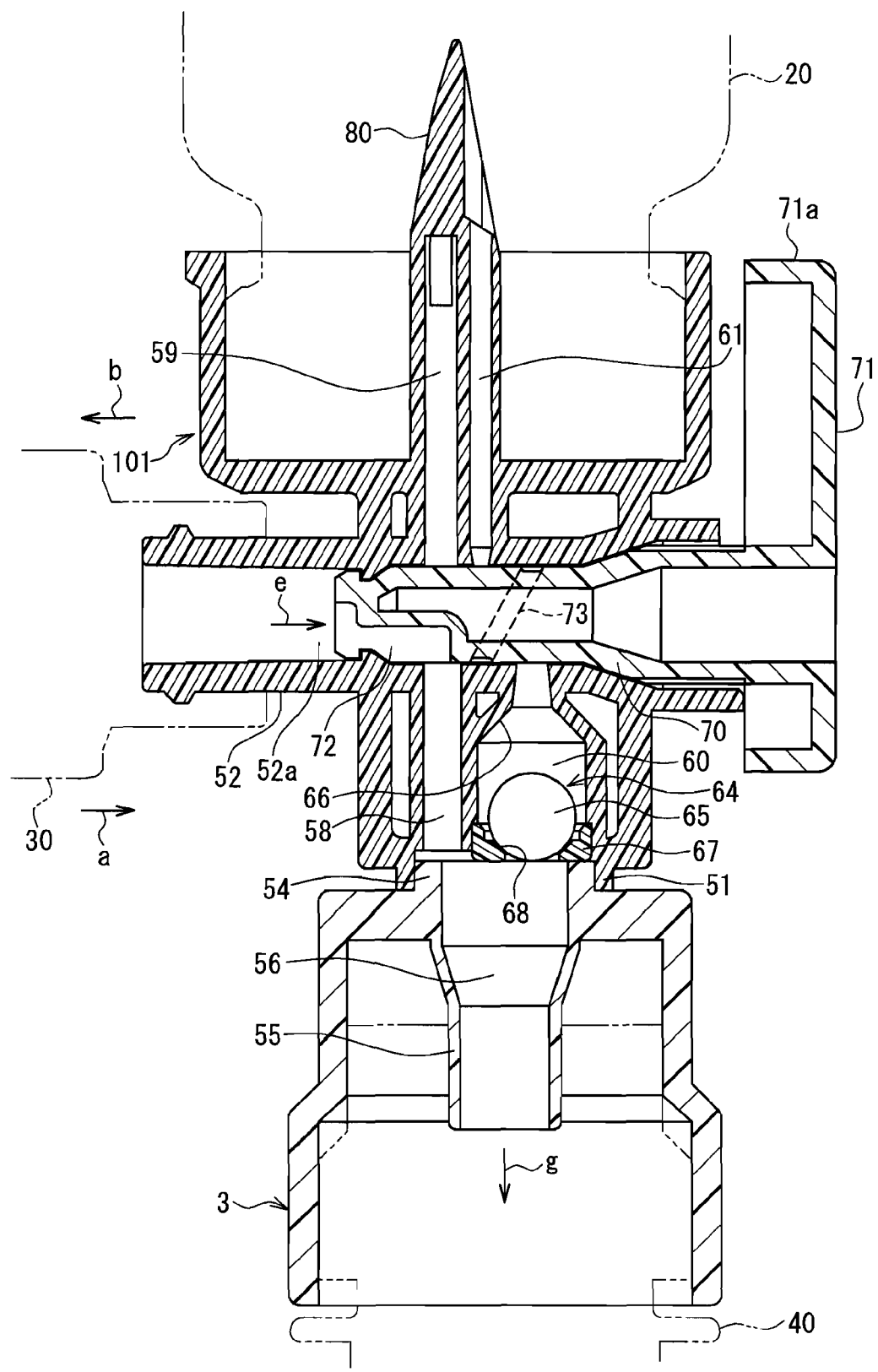
FIG. 22 is a cross-sectional view showing a state in which the drug solution that has been drawn into the syringe 30 is injected into the drug solution bag 10, according to Embodiment 2 of the present invention.

FIG. 22 is a cross-sectional view showing a state in which the drug solution that has been drawn into the syringe 30 is injected into the drug solution bag 10. In FIG. 22, the vertical relationship between the drug solution bag 10 and the vial 20 is the same as that in the state shown in FIG. 21, and the vial 20 remains positioned on the upper side. In FIG. 22, the setting of the stopcock 70 is different from that in FIG. 21. In FIG. 22, the stopcock 70 has been rotated by rotating the lever 71 from the state shown in FIG. 21. In FIG. 21, the first flow channel 72 is positioned on the upper side, whereas in FIG. 22, the first flow channel 72 is positioned on the lower side. That is to say, in FIG. 22, the stopcock 70 is in the setting that brings the first flow channel 72 into communication with the first hole 58.

In the state shown in FIG. 22, when the piston 31 (FIG. 15) of the syringe 30 is pushed in the direction of arrow "a", the drug solution in the syringe 30 is expelled into the inner space 52a of the horizontal tubular portion 52. The drug solution that has reached the inner space 52a flows in the direction of arrow "e" and passes through the first flow channel 72 and the first hole 58 to reach the inner space 56 of the upright tubular portion 55. The drug solution that has reached the inner space 56 flows to the connecting port 40 as indicated by arrow "g" and is injected into the drug solution bag 10.

In this case, an amount of the drug solution corresponding to the amount by which the piston 31 is pushed is injected into the drug solution bag 10. Therefore, the amount of the drug solution to be injected into the drug solution bag 10 can be adjusted by adjusting the amount by which the piston 31 is pushed while looking at the scale on the cylinder 32. That is to say, a required amount of the drug solution can be injected into the drug solution bag 10 with precision.

A required amount of the drug solution can be injected into the drug solution bag 10 through the process as described above. The drug solution in the drug solution bag 10 will be administered into the body via a tube with a needle with which the port portion 60 (FIG. 14) is pierced.

In the present embodiment, an example in which the syringe 30 (FIG. 15) and the connector main body 101 are separate components has been described. However, a configuration in which the cylinder portion 32 of the syringe 30 and the connector main body 101 are integral with each other also may be employed. This is the same as Embodiment 1.

Moreover, in the present embodiment, as shown in FIG. 16, the lever 71 extended from the stopcock 70 is formed on the stopcock 70. It is possible to determine the status of the flow channel setting within the connector 100 from the orientation of the lever 71.

Specifically, in FIG. 19, the end portions on the horizontal tubular portion 52 side of the second hole 59 and the fourth hole 61, which are positioned on the vial 20 side, are obstructed by the side face of the stopcock 70, and no liquid flows into the vial 20. Meanwhile, the leading end 71a of the lever 71 points to the vial 20 side. This means that the leading end 71a of the lever 71 indicates the side on which liquid flow is stopped. Therefore, it is possible to determine that the connector 100 is in a setting that stops liquid transfer to the vial 20 side by observing the orientation of the leading end 71a of the lever 71.

In FIG. 20, the end portion on the horizontal tubular portion 52 side of the first hole 58, which is positioned on the drug solution bag 10 side, is obstructed by the side face of the stopcock 70, and a liquid in the syringe 30 does not flow to the drug solution bag 10 side. Meanwhile, the leading end 71a of the lever 70 points to the port portion 40 side of the drug solution bag 10. This means that the leading end 71a of the lever 71 indicates the side on which liquid flow is stopped. Accordingly, it is possible to determine that the connector 100 is in a setting that stops liquid transfer to the drug solution bag 10 side by observing the orientation of the leading end 71a of the lever 70.

Therefore, it is possible to determine readily which of the drug solution bag 10 side and the vial 20 side the connector 100 stops liquid transfer to/from by observing the orientation of the leading end 71a of the lever 71.

Moreover, the orientation of the leading end 71a of the lever 71 may be reversed from that of the example shown in FIG. 19. In this case, the leading end 71a of the lever 71 in FIG. 19 will point to the connecting port 40 side of the drug solution bag 10, and the leading end 71a of the lever 71 in FIG. 20 will point to the vial 20 side. That is to say, the leading end 71a of the lever 71 indicates the side on which liquid transfer is enabled. Accordingly, in this case, it is possible to readily determine which of the drug solution bag 10 side and the vial 20 side the connector 100 enables transfer to/from by observing the orientation of the leading end 71a of the lever 71.

Moreover, in Embodiments 1 and 2, two types of the first and second flow channels formed in the stopcock have been described. However, one of the first flow channel and the second flow channel of Embodiment 1 may be replaced with the flow channel of Embodiment 2. Also, one of the first flow channel and the second flow channel of Embodiment 2 may be replaced with the flow channel of Embodiment 1. For example, although the first flow channel 33 of Embodiment 1 is described as an L-shaped flow channel, this L-shaped flow channel may be replaced with a groove-like flow channel like the first flow channel 72 of Embodiment 2.

Moreover, in the present embodiment, an example in which the check valve 64 includes the ball 65, the inclined surface 66, and the inclined surface 68 has been described. However, other structures may be employed. Furthermore, although an example in which the check valve 64 is provided in the third hole 60 has been described, the check valve can be provided in at least one of the third hole 60 and the fourth hole 61. For example, it is possible to provide the check valve in the fourth hole 61 when the fourth hole 61 has a larger diameter and a smaller check valve is used.

Industrial Applicability

As described above, the connector according to the present invention is capable of injecting a required amount of drug solution into a drug solution bag with precision and, therefore, is useful as, in particular, a medical connector that can be interposed between a drug solution bag and a vial to inject a pharmaceutical preparation in the vial into the drug solution bag.

REFERENCE SIGNS LIST

1, 100 connector
2, 101 connector main body
3 first connecting portion
4, 57 open portion
5, 70 stopcock
8, 71 lever
8a, 71a leading end of lever
11, 49 connecting port
12 lever lock
16, 52 horizontal tubular portion (tubular portion)
25, 55 upright tubular portion
26 shield
30 syringe
31 piston
32 cylinder
33, 72 first flow channel
34, 35 opening
36, 73 second flow channel
37, 58 first hole
38, 60 third hole
39 hydrophobic filter
43, 59 second hole
44, 61 fourth hole
46 protrusion
64 check valve

The invention claimed is:

1. A connector comprising:
a connector main body provided with a tubular portion; and
a stopcock that is fitted in the tubular portion so as to be rotatable around an axis of the tubular portion,
wherein one end of the tubular portion is sealed with the stopcock that is fitted in the tubular portion,
a first flow channel and a second flow channel are formed in the stopcock,
a first hole, a second hole, a third hole, and a fourth hole are formed in the connector main body,
the first, the second, the third, and the fourth holes are holes that bring an inner space of the tubular portion into communication with an external space of the connector main body,
the first, the second, the third, and the fourth holes are open to an inner circumferential surface of the tubular portion and facing the stopcock, and
the connector is configured to switch between a first setting that brings the inner space of the tubular portion into communication with the first hole via the first flow channel and a second setting that brings the inner space of the tubular portion into communication with the second hole via the first flow channel and brings the third hole into communication with the fourth hole via the second flow channel by rotating the stopcock.

2. The connector according to claim 1,
wherein a first connecting portion and a second connecting portion are provided in the connector main body,
connecting ports are formed in the first and the second connecting portions,
the first and the third holes are in communication with a space in the first connecting portion, and
the second and the fourth holes are in communication with a space on the connecting port side of the second connecting portion.

3. The connector according to claim 2, wherein the first connecting portion comprises a lever lock that is integral with the connecting port formed in the first connecting portion.

4. The connector according to claim 2, wherein the second connecting portion has a protrusion protruding from an inner circumferential surface of the connecting port formed in the second connecting portion.

5. The connector according to claim 2, wherein the first connecting portion has a portion covered with a shield that can open and close by extension and retraction.

6. The connector according to claim 1, wherein the first flow channel is a recess formed in a side face of the stopcock, the recess extending to a leading end face of the stopcock and forming a notch in the leading end face of the stopcock.

7. The connector according to claim 1, wherein both ends of the second flow channel are located at mutually different positions in an axial direction and in a circumferential direction of the stopcock.

8. The connector according to claim 7, wherein the second flow channel is a recess formed in a side face of the stopcock so as to have a spiral shape.

9. The connector according to claim 1, wherein the first flow channel is a hole that brings an opening formed on a leading end side of the stopcock into communication with an opening formed in a side face of the stopcock.

10. The connector according to claim 1, wherein the second flow channel is a penetrating flow channel that passes through the stopcock in a radial direction of the stopcock.

11. The connector according to claim 10, wherein a hydrophobic filter is provided in at least one of the third hole, the penetrating flow channel, and the fourth hole.

12. The connector according to claim 1,
wherein a check valve is provided in at least one of the third hole and the fourth hole, and when the stopcock is set to the second setting that brings the third hole into communication with the fourth hole via the second flow channel, liquid transfer through the third hole and the fourth hole is stopped by the check valve.

13. The connector according to claim 1, wherein a graduated syringe comprising a cylinder and a movable piston is integrally formed on the other end side of the tubular portion.

14. The connector according to claim 1,
wherein a lever extended from the stopcock is formed on the stopcock, and
the lever is disposed in such a manner that:
when the stopcock is set to the first setting that brings the inner space of the tubular portion into communication with the first hole via the first flow channel, a leading end of the extended lever points to an external space side communicating with the first hole, and
when the stopcock is set to the second setting that brings the inner space of the tubular portion into communication with the second hole via the first flow channel, the leading end of the extended lever points to an external space side communicating with the second hole.

15. The connector according to claim 1,
wherein a lever extended from the stopcock is formed on the stopcock, and the lever is disposed in such a manner that:
when the stopcock is set to the first setting that brings the inner space of the tubular portion into communication with the first hole via the first flow channel, a leading end of the extended lever points to an external space side communicating with the second hole, and
when the stopcock is set to the second setting that brings the inner space of the tubular portion into communication with the second hole via the first flow channel, the leading end of the extended lever points to an external space side communicating with the first hole.

16. The connector according to claim 1, wherein the connector is configured to switch between a first position where the third hole is brought into communication with the fourth hole via the second flow channel and a second position where the third hole does not communicate with the fourth hole via the second channel.

\* \* \* \* \*